US010415100B2

(12) United States Patent
Merkoçi Hyka et al.

(10) Patent No.: US 10,415,100 B2
(45) Date of Patent: Sep. 17, 2019

(54) METHODS FOR DETECTING TARGET DNA SEQUENCES

(71) Applicant: VETGENOMICS, S.L., Barcelona (ES)

(72) Inventors: Arben Merkoçi Hyka, Barcelona (ES); Alfredo De La Escosura Muñiz, Barcelona (ES); Lorena Serrano Peralta, Barcelona (ES); Laura Altet Sanahujes, Barcelona (ES); Olga Francino Martí, Barcelona (ES)

(73) Assignee: VETGENOMICS, S.L., Barcelona (ES)

( * ) Notice: Subject to any disclaimer, the term of this patent is extended or adjusted under 35 U.S.C. 154(b) by 69 days.

(21) Appl. No.: 15/324,188

(22) PCT Filed: Jul. 9, 2015

(86) PCT No.: PCT/EP2015/065742
§ 371 (c)(1),
(2) Date: Jan. 5, 2017

(87) PCT Pub. No.: WO2016/005517
PCT Pub. Date: Jan. 14, 2016

(65) Prior Publication Data
US 2017/0175208 A1 Jun. 22, 2017

(30) Foreign Application Priority Data
Jul. 9, 2014 (EP) .................................... 14382266

(51) Int. Cl.
*C12Q 1/6893* (2018.01)
*C12Q 1/6844* (2018.01)
*C12Q 1/6804* (2018.01)
*G01N 21/78* (2006.01)
*G01N 33/53* (2006.01)
*G01N 21/75* (2006.01)

(52) U.S. Cl.
CPC ......... *C12Q 1/6893* (2013.01); *C12Q 1/6804* (2013.01); *C12Q 1/6844* (2013.01); *G01N 21/78* (2013.01); *G01N 33/5308* (2013.01); *C12Q 2600/166* (2013.01); *G01N 2021/752* (2013.01); *G01N 2021/757* (2013.01); *G01N 2333/44* (2013.01); *G01N 2800/26* (2013.01); *Y02A 50/55* (2018.01)

(58) Field of Classification Search
CPC ............ C12Q 1/6844; C12Q 2521/507; C12Q 2527/101; C12Q 2563/113; C12Q 2563/137; C12Q 1/6804; C12Q 1/6893; C12Q 2600/166; G01N 2021/757; G01N 2333/44; G01N 33/5308; Y02A 50/55
See application file for complete search history.

(56) References Cited

U.S. PATENT DOCUMENTS

2012/0129173 A1* 5/2012 Piepenburg .......... C12Q 1/6806
435/6.11

FOREIGN PATENT DOCUMENTS

| EP | 1759012 B1 | 5/2013 |
| WO | 2011038197 A1 | 3/2011 |
| WO | 2011112068 A1 | 9/2011 |
| WO | WO-2015006755 A2 * | 1/2015 ........... C12Q 1/6844 |

OTHER PUBLICATIONS

Pumera, M. et al., Magnetically Trigged Direct Electrochemical Detection of DNA Hybridization Using Au67 Quantum Dot as Electrical Tracer, Langmuir, vol. 21, pp. 9625-9629 (Year: 2005).*
Lermo, A. et al., Biosens. Bioelectr., vol. 22, Supplementary material, pp. 1-11 (Year: 2007).*
Stratagene Catalog, p. 39 (Year: 1988).*
Srivastava, A. et al., Real-Time PCR to Quantify Leishmania donovani in Hamsters, J. Parasitol., vol. 99, pp. 145-150 (Year: 2013).*
GenBank Accession No. Z35272 (Year: 1994).*
Piepenburg, O. et al., DNA Detection Using Recombination Proteins, PLoS Biol., vol. 4(7), e204, pp. 1-14 (Year: 2006).*
Abera, A., et al., "Quantitative lateral flow immunosensor using carbon nanotubes as label", "Analytical Methods", Aug. 26, 2010, pp. 1819-1822, vol. 2.
Adams, E.R., et al., "Development of a Reverse Transcriptase Loop-Mediated Isothermal Amplification (LAMP) Assay for the Sensitive Detection of Leishmania Parasites in Clinical Samples", "The American Journal of Tropical Medicine and Hygiene", 2010, pp. 591-596, vol. 82, No. 4.
Ambrosi, A., et al., "Double-Codified Gold Nanolabels for Enhanced Immunoanalysis", "Analytical Chemistry", Jul. 15, 2007, pp. 5232-5240, vol. 79, No. 14.
Aragay, G., et al., "Recent Trends in Macro-, Micro-, and Nanomaterial-Based Tools and Strategies for Heavy-Metal Detection", "Chemical Reviews", 2011, pp. 3433-3458, vol. 111.
"Presentation of Biogal Company", Jan. 21, 2014.
Craw, P., et al., "Isothermal Nucleic Acid Amplification Technologies for Point-of-Care Diagnostics: a Critical Review", "Lab Chip", 2012, pp. 2469-2486, vol. 12.
Dantas-Torres, F., "Canine leishmaniosis in South America", "Parasites & Vectors; Proceedings from the 4th International Canine Vector-Borne Disease Symposium", Mar. 26, 2009, vol. 2, Supplement 1.
Da Silveira Neto, O., et al., "Design of primer pairs for species-specific diagnosis of Leishmania (Leishmania) infantum chagasi using PCR", "Revista Brasileira de Parasitologia Veterinria", Jul. 2012, pp. 304-307, vol. 21, No. 3.

(Continued)

*Primary Examiner* — Teresa E Strzelecka
(74) *Attorney, Agent, or Firm* — Hultquist, PLLC; Steven J. Hultquist

(57) ABSTRACT

The invention relates to methods for detecting target DNA sequences, particularly for detecting *Leishmania* infection, comprising a recombinase-polymerase isothermal amplification and detection by electrochemistry. The invention also relates to kits and oligonucleotides for performing said methods.

18 Claims, 12 Drawing Sheets
Specification includes a Sequence Listing.

(56) References Cited

OTHER PUBLICATIONS

Deborggraeve, S., et al., "A Simplified and Standardized Polymerase Chain Reaction Format for the Diagnosis of Leishmaniasis", "Journal of Investigative Dermatology", Sep. 24, 2008, pp. 1565-1572, No. JID 2008:198.

Defever, T., et al., "Real-Time Electrochemical Monitoring of the Polymerase Chain Reaction by Mediated Redox Catalysis", "Journal of the American Chemical Society", Jul. 28, 2009, pp. 11433-11441, vol. 131.

De La Escosura-Muniz, A., et al., "Immunosensing using nanoparticles", "Materials Today", Jul.-Aug. 2010, pp. 24-34, vol. 13, No. 7-8.

Del Rio, J.S., et al., "Electrochemical detection of Francisella tularensis genomic DNA using solid-phase recombinase polymerase amplifcation", "Biosensors and Bioelectronics", Nov. 26, 2013, pp. 674-678, vol. 54.

Dominguez Renedo, O., et al., "Recent developments in the field of screen-printed electrodes and their related applications", "Talanta", 2007, pp. 202-219, vol. 73.

Drummond, T.G., et al., "Electrochemical DNA sensors", "Nature Biotechnology", Oct. 2003, pp. 1192-1199, vol. 21, No. 10.

Fang, T.H., et al., "Real-time PCR microfluidic devices with concurrent electrochemical detection", "Biosensors and Bioelectronics", 2009, pp. 2131-2136, vol. 24.

Ferguson, B.S., et al., "Integrated Microfluidic Electrochemical DNA Sensor", "Analytical Chemistry", Aug. 1, 2009, pp. 6503-6508, vol. 81, No. 15.

Ferguson, B.S., et al., "Genetic Analysis of H1N1 Influenza Virus from Throat Swab Samples in a Microfluidic System for Point-of-Care Diagnostics", "Journal of the American Chemical Society", Jun. 15, 2011, pp. 9129-9135, vol. 133, No. 23.

Francino, O., et al., "Advantages of real-time PCR assay for diagnosis and monitoring of canine leishmaniosis", "Veterinary Parasitology", 2006, pp. 214-221, vol. 137.

Gardeniers, J.G.E., "Lab-on-a-chip systems for biomedical and environmental monitoring", "Analytical and Bioanalytical Chemistry", 2004, pp. 1700-1703, vol. 378.

He, Y., et al., "Ultrasensitive nucleic acid biosensor based on enzymegold nanoparticle dual label and lateral flow strip biosensor", "Biosensors and Bioelectronics", Sep. 9, 2010, pp. 2018-2024, vol. 26.

Heid, Christian A., et al., "Real Time Quantitative PCR", "Genome Research", 1996, pp. 986-994, vol. 6.

Higuchi, R., et al., "Kinetic PCR Analysis: Real-time Monitoring of DNA Amplification Reactions", "Nature Bio/Technology", Sep. 1993, pp. 1026-1030, vol. 11.

Holland, C.A., et al., "Point-of-care molecular diagnostic systems past, present and future", "Current Opinion in Microbiology", Aug. 10, 2005, pp. 504-509, vol. 8.

Horng, Y-T., et al., "Development of an improved PCR-ICT hybrid assay for direct detection of Legionellae and Legionella pneumophila from cooling tower water specimens", "Water Research", 2006, pp. 2221-2229, vol. 40.

Hsieh, K., et al., "Rapid, Sensitive, and Quantitative Detection of Pathogenic DNA at the Point of Care via Microfluidic Electrochemical Quantitative Loop-Mediated Isothermal Amplification (MEQ-LAMP)", "Angewandte Chemie International Edition", May 14, 2012, pp. 4896-4900, vol. 51, No. 20.

Jung, Y.L., et al., "Direct colorimetric diagnosis of pathogen infections by utilizing thiol-labeled PCR primers and unmodified gold nanoparticles", "Biosensors and Bioelectronics", Jan. 18, 2010, pp. 1941-1946, vol. 25.

Kaewphinit, T., et al., "Detection of *Mycobacterium tuberculosis* by Using Loop-Mediated Isothermal Amplification Combined with a Lateral Flow Dipstick in Clinical Samples", "BioMed Research International", 2013, pp. 1-6; http://dx.doi.org/10.1155/2013/926230, vol. 2013.

Kersting, S., et al., "Rapid detection of Plasmodium falciparum with isothermal recombinase polymerase amplification and later flow analysis", "Malaria Journal", 2014, pp. 1-9, vol. 13, No. 99.

Kivlehan, F., et al., "Real-time electrochemical monitoring of isothermal helicase-dependent amplification of nucleic acids", "Analyst", 2011, pp. 3635-3642, vol. 136.

Kuan, G.C., et al., "Gold-nanoparticles based electrochemical DNA sensor for the detection of fish pathogen Aphanomyces invadans", "Talanta", Sep. 19, 2013, pp. 312-317, vol. 117.

Kuang, H., et al., "Rapid DNA detection by interface PCR on nanoparticles", "Biosensors and Bioelectronics", 2011, pp. 2495-2499, vol. 26.

Lagally, E.T., et al., "Fully integrated PCR-capillary electrophoresis microsystem for DNA analysis", "Lab on a Chip", Nov. 21, 2001, pp. 102-107, vol. 1.

Laurent, T., et al., "Identification of Old World *Leishmania* spp. by specific polymerase chain reaction amplification of cysteine proteinase B genes and rapid dipstick detection", "Diagnostic Microbiology and Infectious Disease", 2009, pp. 173-181, vol. 63.

Coris Bioconcept, "Leishmania OligoC-TesT Brochure", Jan. 2012, pp. 1-2.

Lermo, A., et al., "In situ DNA amplification with magnetic primers for the electrochemical detection of food pathogens", "Biosensors and Bioelectronics", 2007, pp. 2010-2017, vol. 22.

Liu, Y., et al., "DNA Amplification and Hybridization Assays in Integrated Plastic Monolithic Devices", "Analytical Chemistry", Jul. 1, 2002, pp. 3063-3070, vol. 74, No. 13.

Liu, R.H., et al., "Self-Contained, Fully Integrated Biochip for Sample Preparation, Polymerase Chain Reaction Amplification, and DNA Microarray Detection", "Analytical Chemistry", Apr. 1, 2004, pp. 1824-1831, vol. 76, No. 7.

Llebana, S., et al., "Magneto Immunoseparation of Pathogenic Bacteria and Electrochemical Magneto Genosensing of the Double-Tagged Amplicon", "Analytical Chemistry", Jul. 15, 2009, pp. 5812-5820, vol. 81, No. 14.

Lou, S. et al., "A gold nanoparticle-based immunochromatographic assay: The influence of nanoparticulate size", "Analyst", 2012, pp. 1174-1181, vol. 137.

Medina-Sanchez, M., et al., "On-chip electrochemical detection of CdS quantum dots using normal and multiple recycling flow through modes", "Lab Chip", 2012, pp. 2000-2005, vol. 12.

Mir, M., et al., "Integrated electrochemical DNA biosensors for lab-on-a-chip devices", "Electrophoresis", 2009, pp. 3386-3397, vol. 30.

Mohan, S., et al., "Nano Structured Nickel Oxide based DNA Biosensor for Detection of Visceral Leishmaniasis (Kala-azar)", "Analyst", Jul. 7, 2011, pp. 2845-2851, vol. 136, No. 13.

Mugasa, C.M., et al., "Simplified molecular detection of Leishmania parasites in various clinical samples from patients with leishmaniasis", "Parasites & Vectors", 2010, pp. 1-6, vol. 3, No. 13.

Nagatini, N., et al., "Semi-real time electrochemical monitoring for influenza virus RNA by reverse transcription loop-mediated isothermal amplification using a USB powered portable potentiostat", "Analyst", 2011, pp. 5143-5150, vol. 136.

Niemz, A., et al., "Point-of-care nucleic acid testing for infectious disease", "Trends in Biotechnology", May 2011, pp. 240-250, vol. 29, No. 5.

Otranto, D., et al., "The prevention of canine leishmaniasis and its impact on public health", "Trends in Parasitology", Jul. 2013, pp. 339-345, vol. 29, No. 7.

Palchetti, I., et al., "Electroanalytical biosensors and their potential for food pathogen and toxin detection", "Analytical and Bioanalytical Chemistry", Feb. 17, 2008, pp. 455-471, vol. 391.

Parolo, C., et al., "Simple paper architecture modifications lead to enhanced sensitivity in nanoparticle based lateral flow immunoassays", "Lab Chip", 2013, pp. 386-390, vol. 13.

Parolo, C., et al., "Enhanced lateral flow immunoassay using gold nanoparticles loaded with enzymes", "Biosensors and Bioelectronics", 2013, pp. 412-416, vol. 40.

Perfezou, M., et al., "Cancer detection using nanoparticle-based sensors", "Chemical Society Reviews", 2012, pp. 2606-2622, vol. 41.

(56) References Cited

OTHER PUBLICATIONS

Piepenburg, O., et al., "DNA Detection Using Recombination Proteins", "PLoS Biology", Jul. 2006, pp. 1115-1121, vol. 4, No. 7.
Posthuma-Trumpie, G.A., et al., "Lateral flow (immuno)assay: its strengths, weaknesses, opportunities and threats. A literature survey.", "Analytical and Bioanalytical Chemistry", 2009, pp. 569-582, vol. 393.
Prompamorn, P, et al., "The development of loop-mediated isothermal amplification combined with lateral flow dipstick for detection of Vibrio parahaemolyticus", "Letters in Applied Microbiology", 2011, pp. 344-351, vol. 52.
Puertas, S., et al., "Designing novel nano-immunoassays: antibody orientation versus sensitivity", "Journal of Physics D: Applied Physics", Nov. 11, 2010, pp. 1-9; doi:10.1088/0022-3727/43/47/474012, vol. 43.
Rodgers, M.R., et al., "Amplification of Kinetoplast DNA as a Tool in the Detection and Diagnosis of Leishmania", "Experimental Parasitology", 1990, pp. 267-275, vol. 71.
Shu, H., et al., "Novel electrochemical aptamer biosensor based on gold nanoparticles signal amplification for the detection of carcinoembryonic antigen", "Electrochemistry Communications", Oct. 5, 2013, pp. 15-19, vol. 37.
Shukla, S., et al., "Development of a liposome-based immunochromatographic strip assay for the detection of *Salmonella*", "Analytical and Bioanalytical Chemistry", 2011, pp. 2581-2590, vol. 401.
Solano-Gallego, L., et al., "Directions for the diagnosis, clinical staging, treatment and prevention of canine leishmaniosis", "Veterinary Parasitology", 2009, pp. 1-18, vol. 165.
Srividya, G., et al., "Diagnosis of visceral leishmaniasis: developments over the last decade", "Parasitology Research", 2012, pp. 1065-1078, vol. 110.
Storhoff, J.J., et al., "One-Pot Colorimetric Differentiation of Polynucleotides with Single Base Imperfections Using Gold Nanoparticle Probes", "Journal of the American Chemical Society", 1998, pp. 1959-1964, vol. 120.
Tang, D-Q., et al., "One-Step Electrochemical Immunoassay for Carcinoembryonic Antigen in Human via Back-Filling Immobilization of Gold Nanoparticles on DNA-Modified Gold Electrodes", "Electroanalysis", 2006, pp. 2194-2201, vol. 18, No. 22.
Tang, D. et al., "Magnetic nanogold microspheresbased detection of aflatoxin B2 in food", "Biosensors and Bioelectronics", Aug. 4, 2009, pp. 514-518, vol. 25.
Thielbeer, F., et al., "Zeta Potential Mediated Reaction Monitoring on Nano and Microparticles", "Bioconjugate Chemistry", 2011, pp. 144-150, vol. 22.
Tlili, C., et al., "Bacteria Screening, Viability, and Con!rmation Assays Using Bacteriophage-Impedimetric/Loop-Mediated Isothermal Ampli!cation Dual-Response Biosensors", "Analytical Chemistry", 2013, pp. 4893-4901, vol. 85.
Torres-Chavolla, E., et al., "Nanoparticle based DNA biosensor for tuberculosis detection using thermophilic helicasedependent", "Biosensors and Bioelectronics", May 6, 2011, pp. 4614-4618, vol. 26.
Turkevich, J., et al., "A Study of the Nucleation and Growth Processes in the Synthesis of Colloidal Gold", "Discussions of the Faraday Society", 1951, pp. 55-75, vol. 11.
University of Texas Medical Branch Institute for Human Infections & Immunity, "utmb Health Update", Jan. 2014, No. 9.
Wang, J., "Electrochemical biosensors: Towards point-of-care cancer diagnostics", "Biosensors and Bioelectronics", 2006, pp. 1887-1892, vol. 21.
Wang, C., et al., "Signal-on impedimetric electrochemical DNA sensor using dithiothreitol modified gold nanoparticle tag for highly sensitive DNA detection", "Analytica Chimica Acta", Sep. 14, 2013, pp. 36-43, vol. 799.
Weiss, J.B., "DNA Probes and PCR for Diagnosis of Parasitic Infections", "Clinical Microbiology Reviews", Jan. 1995, pp. 113-130, vol. 8, No. 1.
Wilson, S.M., "DNA-based methods in the detection of Leishmania parasites: field applications and practicalities", "Annals of Tropical Medicine and Parasitology", 1995, pp. 95-100, vol. 89, No. 1.
Xie, S., et al., "Development of an electrochemical method for Ochratoxin A detection based on aptamer and loop-mediated isothermal amplifcation", "Biosensors and Bioelectronics", 2014, pp. 324-329, vol. 55.
Yan, Y., et al., "A Simple and Highly Sensitive Electrochemical Biosensor for microRNA Detection Using Target-Assisted Isothermal Exponential Amplification Reaction", "Electroanalysis", Sep. 18, 2013, pp. 2354-2359, vol. 25, No. 10.
Yeung, S.S.W., et al., "Electrochemistry-Based Real-Time PCR on a Microchip", "Analytical Chemistry", 2008, pp. 363-368, vol. 80.
Yin, H., et al., "Electrochemical determination of microRNA-21 based on graphene, LNA integrated molecular beacon, AuNPs and biotin multifunctional bio bar codes and enzymatic assay system", "Biosensors and Bioelectronics", Jan. 23, 2012, pp. 247-253, vol. 33.
Zanoli, L.M., et al., "Isothermal Amplification Methods for the Detection of Nucleic Acids in Microfluidic Devices", "Biosensors", Dec. 27, 2012, pp. 18-43, vol. 3.
Zhan, F. et al., "Rapid and sensitive electrochemiluminescence detection of rotavirus by magnetic primer based reverse transcription-polymerase reaction", "Analytica Chimica Acta", 2013, pp. 71-77, vol. 761.
Zhao W. et al., "Paper-Based Bioassays Using Gold Nanoparticle Coloimetric Probes", "Analytical Chemistry", Nov. 15, 2008, pp. 8431-8437, vol. 80, No. 22.
Zhu, X., et al., "High Sensitive Detection of Cry1Ab Protein Using a Quantum Dot-Based Fluorescence-Linked Immunosorbent Assay", "Journal of Agricultural and Food Chemistry", Feb. 17, 2011, pp. 2184-2189, vol. 59.
Zou, Z., et al., "Quantum Dot-Based Immunochromatographic Fluorescent Biosensor for Biomonitoring Trichloropyridinol, a Biomarker of Exposure to Chlorpyrifos", "Analytical Chemistry", Jun. 15, 2010, pp. 5125-5133, vol. 82, No. 12.
Daniel, M.C., et al., "Gold Nanoparticles: Assembly, Supramolecular Chemistry, Quantum-Size-Related Properties, and Applications toward Biology, Catalysis, and Nanotechnology", "Chem. Rev.", 2004, pp. 293-346, vol. 104, Publisher: American Chemical Society.
Muniz, A., et al., "Electrochemical analysis with nanoparticle-based biosystems", "Trends in Analytical Chemistry", 2008, pp. 568-584, vol. 27, No. 7, Publisher: Elsevier, Ltd.
Muniz, A., et al., "Immunosensing Using Nanoparticles", "Materials Today", 2010, pp. 24-34, vol. 13, No. 7-8.
Muniz, A., et al., "Nanoparticles for Proteins and Cells Detection", "G.I.T. Laboratory Journal", 2012, pp. 21-23, vol. 1—Dec. 2012, Publisher: Wiley-VCH GmbH & Co.
Muniz, A., et al., "Magnetic Bead/Gold Nanoparticle Double-Labeled Primers for Electrochemical Detection of Isothermal Amplified Leishmania DNA", "Small", 2016, pp. 205-213, vol. 12, No. 2, Publisher: Wiley-VCH Verlag GmbH & Co.
Seydack, M., "Nanoparticle labels in immunosensing using optical detection methods", "Biosensors & Bioelectronics", 2005, pp. 2454-2469, vol. 20, Publisher: Elsevier.
Wang, J., et al., "Electrochemical detection of DNA immobilized on gold colloid particles modified self-assembled monolayer electrode with silver nanoparticle label", "Journal of Pharmaceutical and Biomedical Analysis", 2003, pp. 1117-1125, vol. 33, Publisher: Elsevier.
Wang, J., et al., "Electrochemical stripping detection of DNA hybridization based on cadmium sulfide nanoparticle tags", "Electrochemistry Communications", 2002, pp. 722-726, vol. 4, Publisher: Elsevier.
Wang, J., et al., "Particle-based detection of DNA hybridization using electrochemical stripping measurements of an iron tracer", "Analytica Chimica Acta", 2003, pp. 149-155, vol. 482, Publisher Elsevier.

\* cited by examiner

SEQUENCE LISTING

<160> NUMBER OF SEQ ID NOS: 5

<210> SEQ ID NO 1
<211> LENGTH: 31
<212> TYPE: DNA
<213> ORGANISM: Artificial Sequence
<220> FEATURE:
<223> OTHER INFORMATION: K6F primer

```
<400> SEQUENCE: 1
cttttctggt cctccgggta ggggcgttct g                              31

<210> SEQ ID NO 2
<211> LENGTH: 37
<212> TYPE: DNA
<213> ORGANISM: Artificial Sequence
<220> FEATURE:
<223> OTHER INFORMATION: K3R primer

<400> SEQUENCE: 2
ccacccggcc ctattttaca ccaacccca gtttccc                         37

<210> SEQ ID NO 3
<211> LENGTH: 33
<212> TYPE: DNA
<213> ORGANISM: Artificial Sequence
<220> FEATURE:
<223> OTHER INFORMATION: 18s 1F primer

<400> SEQUENCE: 3
ctgcgaatgg ctcattaaat cagttatggt tcc                            33

<210> SEQ ID NO 4
<211> LENGTH: 35
<212> TYPE: DNA
<213> ORGANISM: Artificial Sequence
<220> FEATURE:
<223> OTHER INFORMATION: 18s 1R primer

<400> SEQUENCE: 4
ctgaccgggt tggttttgat ctgataaatg cacgc                          35

<210> SEQ ID NO 5
<211> LENGTH: 15
<212> TYPE: DNA
<213> ORGANISM: Artificial Sequence
<220> FEATURE:
<223> OTHER INFORMATION: polynucleotide spacer

<400> SEQUENCE: 5
atatatatat atata                                                15
```

METHODS FOR DETECTING TARGET DNA SEQUENCES

CROSS-REFERENCE TO RELATED APPLICATIONS

This application is a U.S. national phase under the provisions of 35 U.S.C. § 371 of International Patent Application No. PCT/EP2015/065742 filed Jul. 9, 2015, which in turn claims priority of European Patent Application No. 14382266.6 filed Jul. 9, 2014. The disclosures of such international patent application and European priority patent application are hereby incorporated herein by reference in their respective entireties, for all purposes.

FIELD OF THE INVENTION

The invention relates to methods for detecting target DNA sequences, specifically to the field of diagnostics and, more particular, to methods for detecting *Leishmania* infection comprising a recombinase-polymerase isothermal amplification and detection by electrochemistry.

BACKGROUND OF THE INVENTION

The detection of specific DNA target sequences present in air, food, water, environment or clinical samples is of great significance in the medical, veterinary, microbiology, food and water safety-testing, and environment monitoring fields. The detection for the presence of a specific genetic sequence in a sample can rapidly and correctly identify genetic defects, oncogenic events and bacterial, viral or parasitic agents of concern.

In the field of diagnostics of infectious diseases accurate identification of the causative organism is time-critical. Some rapid, sensitive and specific methods have been developed to replace the time-consuming and limited culture methods.

Diseases transmitted by blood-feeding vectors (parasites) are a growing threat to world health, particularly those affecting pets and transmitted by fleas, ticks, sandflies or mosquitoes (Vector Borne Diseases, VBD). VBD are known by worldwide veterinarians and usually have zoonotic consequences being important for human health.

Pets usually have a main role in the maintenance of zoonotic infections. Major VBD are provoked by *Leishmania, Babesia, Anaplasma, Ehrlichia, Dirofilaria, Borrelia* (Lyme disease), *Rickettsia* and *Hepatozoon*. Several of these are global infections and may cause severe diseases in humans. Pets may play an important role as parasite reservoirs and as sentinels of the infection due to their contact with humans.

One of the most important vector-borne diseases is visceral leishmaniasis which is endemic in 88 countries on 4 continents. The overall prevalence is 12 million people although the population at risk is 350 million. Leishmaniasis is regarded as the most important zoonotic disease within Europe. Zoonotic visceral leishmaniasis, caused by the protozoan *Leishmania infantum* and transmitted by sandfly vectors, is a fatal disease of domestic dogs, wild canids and humans which occurs mainly in the Mediterranean, Middle East and South America. The domestic dog is considered the major host for zoonotic leishmaniasis mainly in Europe. Moreover, leishmaniasis is emerging within non endemic areas and is thus increasingly becoming an important concern both from human public health and animal welfare perspectives due to movement of infected dogs, ongoing climatic change and the consequent extension of the range of the sandfly vector towards more northern latitudes.

Guidelines for canine Leishmaniasis diagnostic include clinical signs, clinicopathological abnormalities and serological status being molecular test of limited use for the need of skilled workers, the high cost and the fact that samples must be send to a reference lab. Moreover, the presence of lower antibody levels is not necessarily indicative of disease and further work-up is necessary to confirm it by other diagnostic methods, being PCR the gold standard.

Several molecular tests capable of direct parasite detection in an inexpensive, quantitative, reliable and friendly to use format to be performed at the clinician (point-of-care, POC) have been developed.

A dipstick format was developed for detection of PCR products by hybridization with a gold-conjugate probe, and a PCR oligochromatographic *leishmania*-specific test is being commercialized using this technology (*Leishmania* OligoC-test, Coris Bioconcept) (Deborggraeve S. et al. 2008. JID, 198:1565-1572). In 2011, the US Food and Drug Administration (FDA) approved the Smart Leish PCR assay (Cepheid USA), a qualitative real-time PCR test for diagnosing individuals with cutaneous leishmaniasis. Both systems did not overcome the limitations of PCR for which sophisticated and expensive equipment is needed to perform the precise and repeated heating cycles required.

Mohan (Mohan S. et al. 2011. Analyst, 136: 2845-2851) discloses an electrochemical detection assay for *L. donovani* wherein the genomic DNA of *Leishmania* is extracted and hybridized with a single strand oligonucleotide specific for *L. donovani* that is immobilized onto an ITO/NiO electrode. However, this method has low sensitivity and does not allow detecting double-stranded PCR amplicons.

Sabaté del Rio J. et al. (Sabaté del Rio J. et al. 2014. Biosensors and Bioelectronics, 54:674-678) disclose an electrochemical detection assay for *Francisella tularensis*. However, one of the limitations of this method is the lack of multiplex detection. Furthermore, it requires a DNA hybridization step which increases the analysis time and involves more irreproducibility, loss of sensitivity and false positives due to unspecific absorptions.

Therefore, there is still a need for further POC diagnostic methods for detecting infections by pathogens, particularly for diagnosing leishmaniasis.

BRIEF DESCRIPTION OF THE INVENTION

In a first aspect, the invention relates to an in vitro method for detecting a target DNA sequence in a sample comprising the following steps:
  a) submitting the sample DNA to a recombinase-polymerase isothermal nucleic acid amplification in the presence of a pair of primers capable of specifically amplifying the target DNA sequence wherein the first primer is labelled at the 5' end with a gold nanoparticle and the second primer is labelled at the 5' end with a first member of a binding pair, and
  b) measuring the electrochemical signal produced by the gold nanoparticles forming part of the amplification products obtained in step a) using a screen-printed carbon electrode after capture of the amplification products on the electrode using magnetic beads conjugated to a second member of a binding pair, wherein the detection of an electrochemical signal superior to the background signal indicates the presence of the target DNA sequence in the sample.

In a second aspect, the invention relates to an in vitro method for detecting a target DNA sequence in a sample comprising the following steps:
  a) submitting the sample DNA to a recombinase-polymerase isothermal nucleic acid amplification in the presence of a pair of primers capable of specifically amplifying the target DNA sequence wherein the first primer is labelled at the 5' end with a first member of a first binding pair and the second primer is labelled at the 5' end with a first member of a second binding pair, and wherein said first members of the first and second binding pairs do not substantially cross-react with any second member of any different binding pair, and
  b) measuring the electrochemical signal produced by the gold nanoparticles forming part of the amplification products obtained in step a) using a screen-printed carbon electrode after the first member of a first binding pair is bound to a second member of a first binding pair conjugated to a gold nanoparticle and after capture of the amplification products on the electrode using magnetic beads conjugated to a second member of a second binding pair
wherein the detection of an electrochemical signal superior to the background signal indicates the presence of the target DNA sequence in the sample.

In another aspect, the invention relates to a kit comprising a pair of primers capable of specifically amplifying a target DNA sequence wherein the first primer is labelled at the 5' end with a gold nanoparticle and the second primer is labelled at the 5' end with a first member of a binding pair, and the first member of a binding pair is bound to a second member of a binding pair conjugated to magnetic beads, and wherein said magnetic beads have a size lower than 2.8 μm and are separated from the region of the primer that recognizes the target DNA sequence by a polynucleotide spacer.

In another aspect, the invention relates to a kit comprising:
  (i) a pair of primers capable of specifically amplifying a target DNA sequence wherein the first primer is labelled at the 5' end with a gold nanoparticle and the second primer is labelled at the 5' end with a first member of a binding pair, and
  (ii) a second member of a binding pair conjugated to magnetic beads.

In a further aspect, the invention relates to an in vitro method for diagnosing an infection by a pathogen in a subject comprising detecting the presence of a target DNA sequence from said pathogen in a biological sample of said subject by a method according to the invention.

In a further aspect, the invention relates to an oligonucleotide whose sequence is selected from the group consisting of SEQ ID NO: 1 and SEQ ID NO: 2.

DETAILED DESCRIPTION OF THE INVENTION

Figure 1:
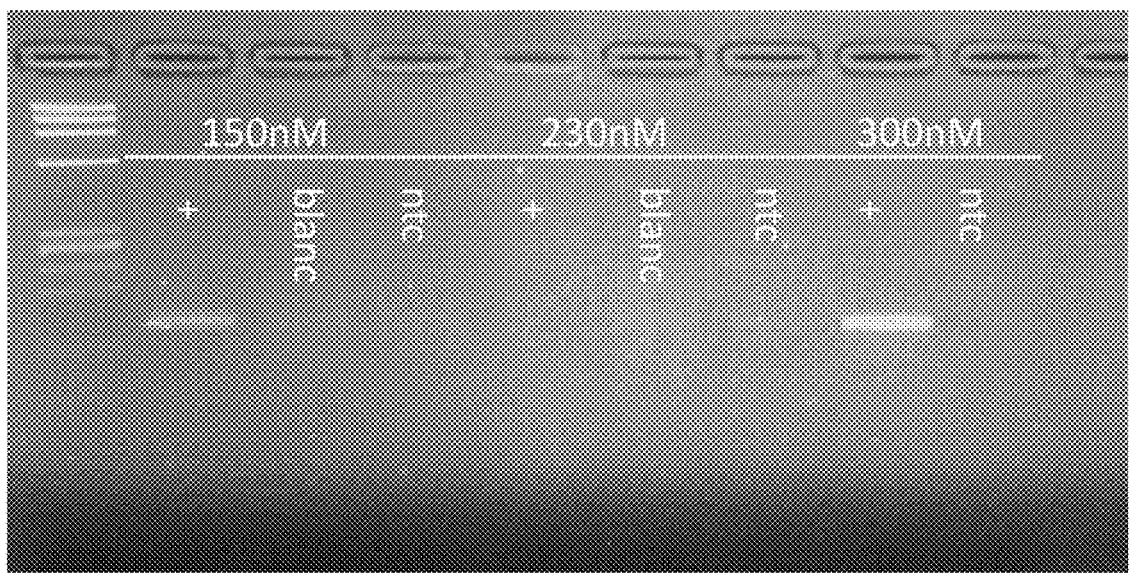
FIG. 1. Optimization of primer concentration of *Leishmania* assay. +, positive sample (DNA of a dog with *Leishmania* infection); blanc, negative sample; ntc, negative template control.

The inventors of the present invention have discovered that the amplification of a target DNA by a recombinase-polymerase isothermal amplification and the detection of the amplified products by electrochemistry allows diagnosing infectious diseases in a more rapid, sensitive and specific way.

Particularly, the inventors propose an assay for *Leishmania* kinetoplast identification that comprises a first step of amplification of the target DNA by a recombinase-polymerase isothermal amplification (RPA) technique. This technique is rapid, cost effective, easy-to-use and more tolerant to inhibitory components from a crude sample compared to PCR. It is a powerful tool for POC diagnostic since it does not have the additional complexity of PCR thermal cycling steps. The amplification step involves the use of labelled primers to generate a double labelled product. The labels of said primers are used in the subsequent step for the detection of the amplified products. An advantage of said labelled primers is that they avoid the use of internal probes for the detection of the amplified products. Probes can be difficult to design when the amplicon has a high polymorphism and the methods of the invention overcome this disadvantage.

The assay involves the amplification of *Leishmania* kinetoplast by RPA with labelled primers combined with the advantages of magnetic purification/preconcentration and the use of gold nanoparticle (AuNPs) tags for the quantitative electrochemical detection of the amplified products. The integration of nanoparticles in one of the strands of the amplicon allows a stable, sensitive and low cost detection. The optimized method allows detecting 0.004 spiked parasites per DNA amplification reaction. This method avoids DNA hybridization biosensing. Furthermore, it is simpler, faster and has less steps than other methods of the prior art.

FIRST METHOD OF THE INVENTION

In a first aspect, the invention relates to an in vitro method (hereinafter referred to as "first method of the invention") for detecting a target DNA sequence in a sample comprising the following steps:
 a) submitting the sample DNA to a recombinase-polymerase isothermal nucleic acid amplification in the presence of a pair of primers capable of specifically amplifying the target DNA sequence wherein the first primer is labelled at the 5' end with a gold nanoparticle and the second primer is labelled at the 5' end with a first member of a binding pair, and
 b) measuring the electrochemical signal produced by the gold nanoparticles forming part of the amplification products obtained in step a) using a screen-printed carbon electrode after capture of the amplification products on the electrode using magnetic beads conjugated to a second member of a binding pair,
wherein the detection of an electrochemical signal superior to the background signal indicates the presence of the target DNA sequence in the sample.

The target DNA sequence can be any DNA sequence. This includes, without limitation, genomic DNA (nuclear DNA, mitochondrial DNA, chloroplast DNA, etc.), and plasmid DNA. An expert in the field can access any target DNA sequence through public databases, for example GenBank. The target DNA sequence can be a nucleic acid from an animal (e.g. human), plant, fungal (e.g. yeast), protozoan, bacterial, or viral species. For example, the target DNA sequence can be present in the genome of an organism of interest. In a particular embodiment the target DNA sequence is specific for the organism of interest, i.e. the target nucleic acid is not found in other organisms or not found in organisms similar to the organism of interest. In a preferred embodiment the target DNA sequence is from a pathogen, particularly is from an infectious organism.

In an embodiment the target DNA sequence is a sequence from bacteria, e.g., Gram-positive or Gram-negative bacteria. Exemplary bacterial species include, without limitation, *Acinetobacter* sp. strain ATCC 5459, *Acinetobacter calcoaceticus, Aerococcus viridans, Bacteroides fragilis, Bordetella pertussis, Bordetella parapertussis, Campylobacter jejuni, Clostridium difficile, Clostridium perfringens, Corynebacterium* sp., *Chlamydia pneumoniae, Chlamydia trachomatis, Citrobacter freundii, Enterobacter aerogenes, Enterococcus gallinarum, Enterococcus faecium, Enterobacter faecalis* (e.g., ATCC 29212), *Escherichia coli* (e.g., ATCC 25927), *Gardnerella vaginalis, Helicobacter pylori, Haemophilus influenzae* (e.g., ATCC 49247), *Klebsiella pneumoniae, Legionella pneumophila* (e.g., ATCC 33495), *Listeria monocytogenes* (e.g., ATCC 7648), *Micrococcus* sp. strain ATCC 14396, *Moraxella catarrhalis, Mycobacterium kansasii, Mycobacterium gordonae, Mycobacterium fortuitum, Mycoplasma pneumoniae, Mycoplasma hominis, Neisseria meningitis* (e.g., ATCC 6250), *Neisseria gonorrhoeae, Oligella urethralis, Pasteurella multocida, Pseudomonas aeruginosa* (e.g., ATCC 10145), *Propionibacterium acnes, Proteus mirabilis, Proteus vulgaris, Salmonella* sp. strain ATCC 31194, *Salmonella typhimurium, Serratia marcescens* (e.g., ATCC 8101), *Staphylococcus aureus* (e.g., ATCC 25923), *Staphylococcus epidermidis* (e.g., ATCC 12228), *Staphylococcus lugdunensis, Staphylococcus saprophyticus, Streptococcus pneumoniae* (e.g., ATCC 49619), *Streptococcus pyogenes, Streptococcus agalactiae* (e.g., ATCC 13813), *Treponema pallidum, Viridans* group streptococci (e.g., ATCC 10556), *Bacillus anthracis, Bacillus cereus, Francisella philomiragia* (GA01-2810), *Francisella tularensis* (LVSB), *Yersinia pseudotuberculosis* (PB 11+), *Yersinia enterocolitica*, 0:9 serotype, and *Yersinia pestis* (P14−). In some embodiments, the target DNA sequence is from a species of a bacterial genus selected from *Acinetobacter, Aerococcus, Bacteroides, Bordetella, Campylobacter, Clostridium, Corynebacterium, Chlamydia, Citrobacter, Enterobacter, Enterococcus, Escherichia, Helicobacter, Haemophilus, Klebsiella, Legionella, Listeria, Micrococcus, Mobilincus, Moraxella, Mycobacterium, Mycoplasma, Neisseria, Oligella, Pasteurella, Prevotella, Porphyromonas, Pseudomonas, Propionibacterium, Proteus, Salmonella, Serratia, Staphylococcus, Streptococcus, Treponema, Bacillus, Francisella*, and *Yersinia*. In another embodiment, the target DNA sequence is from a species of a bacterial genus selected from the group consisting of *Ehrlichia, Rickettsia, Bartonella, Borrelia, Coxiella, Mycoplasma, Chlamydophila* and *Anaplasma*. Particularly, the target DNA sequence is from a bacterial species selected from the group consisting of *Anaplasma platys, Anaplasma phagocytophilum, Ehrlichia canis, Ehrlichia chafensis, Borrelia burgdorferi, Coxiella burnetii, Rickettsia rickettsii, Rickettsia canorii, Rickettsia fells, Rickettsia helvetica, Rickettsia massielae, Rickettsia monacensis, Rickettsia typhi, Bartonella henselae, Bartonella clarridgeiae, Bartonella rochalimae, Bartonella Bartonella birtlesii, Bartonella vinsonii, Mycoplasma ovis, Mycoplasma suis, Mycoplasma haemofelis, Mycoplasma haemocanis, Candidatus Mycoplasma haematoparvum, Candidatus Mycoplasma hamominutum, Candidatus Mycoplasma turicensis* and *Chlamydophila psittacii*. In a preferred embodiment, the target DNA sequence is from a species of a bacterial genus selected from the group consisting of *Ehrlichia* and *Anaplasma*.

In another embodiment, the target DNA sequence is a viral DNA sequence. For example, without limitation, the viral DNA can be from human immunodeficiency virus (HIV), influenza virus, dengue virus, herpes simplex virus, varicella-zoster virus, Epstein-barr virus, cytomegalovirus, papillomavirus, BK virus, JC virus, smallpox, hepatitis B virus, parvovirus, astrovirus, Norwalk virus, coxsackievirus, hepatitis A virus, poliovirus, rhinovirus, severe acute respiratory syndrome virus, hepatitis C virus, yellow fever virus, West Nile virus, rubella virus, hepatitis E virus, Lassa virus, haemorrhagic fever virus, Ebola virus, Marburg virus, measles virus, mumps virus, parainfluenza virus, respiratory syncytial virus, metapneumovirus, Hendra virus, Nipah virus, rabies virus, hepatitis D virus, rotavirus, orbivirus, coltivirus or Banna virus. In another embodiment, the target DNA sequence is from a virus selected from the group consisting of canine distemper virus, canine herpesvirus, feline coronavirus, Beak and feather disease virus (BFDV), polyomavirus and herpesvirus.

In another embodiment, the target DNA sequence is a protozoan DNA sequence. For example, the protozoan DNA sequence can be, without limitation, a DNA sequence from

*Babesia divergens, Babesia bigemina, Babesia equi, Babesia microti, Babesia duncani, Plasmodium* spp., *Leishmania* spp., *Trypanosoma brucei gambiense, Trypanosoma brucei rhodesiense, Trypanosoma cruzi, Entamoeba* spp., *Toxoplasma* spp., *Trichomonas vaginalis,* or *Giardia duodenalis.* In another embodiment, the target DNA sequence is from a species of a protozoan genus selected from the group consisting of *Toxoplasma, Hepatozoon, Neospora, Babesia* and *Theileria*. Preferably, the target DNA sequence is from a protozoan species selected from the group consisting of *Toxoplasma Hepatozoon canis, Hepatozoon fells, Neospora caninum, Babesia gibsoni, Babesia canis, Babesia canis canis, Babesia canis vogeli, Babesia microti, Babesia equi, Babesia rossi* and *Theileria annae*. In a preferred embodiment, the target DNA sequence is from a species of a protozoan genus selected from the group consisting of *Babesia* and *Theileria*. In a more preferred embodiment, the target DNA sequence is from an organism of the Kinetoplastea class.

The Kinetoplastea class is a group of single-cell flagellate protozoa, including a number of parasites responsible for diseases in humans and other animals, as well as various forms found in soil and aquatic environments. They are members of the phylum Euglenozoa and their major distinguishing feature is the presence of a kinetoplast (called kDNA), a dense DNA-containing granule located within the single mitochondrion that contains the mitochondrial genome. The kinetoplast is found at the base of a cell's flagella and is associated to the flagellum basal body by a cytoskeletal structure. The kinetoplast is easily visible in samples stained with DAPI or by the use of FISH with BrdU. Kinetoplastea class includes, without limitation, species of *Trypanosoma* and *Leishmania* genus.

The assay of the present invention targets a conserved region of the *Leishmania* kinetoplast minicircle DNA that is present in about 10,000 copies for parasite. Therefore, in a preferred embodiment the target DNA sequence is a sequence of the kinetoplast, preferably the sequence of the kinetoplast of *Leishmania infantum*. The sequence of the kinetoplast from several *Leishmania infantum* isolates may be found on GenBank. Exemplary DNA sequences from *Leishmania infantum* kinetoplast DNA are, without limitation, sequences with GenBank accession numbers Z35500.1 (dated 9 Sep. 2004), AF169133.1 (dated 1 Dec. 2000), AF103735.1 (dated 2 Jul. 1999), AF103741.1 (dated 2 Jul. 1999), AF169131.1 (dated 1 Dec. 2000), AF169140.1 (dated 1 Dec. 2000), Z35274.1 (dated 15 Jul. 1994), Z35292.1 (dated 18 Jul. 1994), AF184044.1 (dated 30 Nov. 2000), AF190475.1 (dated 30 Nov. 2000), Z35270.1 (dated 15 Jul. 1994), EU437407.1 (dated 31 Jan. 2010), AF188701.1 (dated 30 Nov. 2000), AF190883.1 (dated 27 Oct. 1999), EU437405.1 (dated 31 Jan. 2010), EU437403.1 (dated 31 Jan. 2010), EU437406.1 (dated 31 Jan. 2010), Z35269.1 (dated 15 Jul. 1994), Z35501.1 (dated 9 Sep. 2004), EU437404.1 (dated 31 Jan. 2010), AF190476.1 (dated 30 Nov. 2000), AF190882.1 (dated 27 Oct. 1999), Z35271.1 (dated 15 Jul. 1994), Z35273.1 (dated 15 Jul. 1994) and Z35272.1 (dated 15 Jul. 1994).

In another embodiment, the target DNA sequence is a DNA sequence from a parasite. For example, the parasite DNA sequence can be, without limitation, a DNA sequence from *Acanthamoeba, Balamuthia mandrillaris, Babesia Balantidium coli, Blastocystis, Cryptosporidium, Dientamoeba fragilis, Entamoeba histolytica, Giardia lamblia, Giardia duodenalis, Isospora belli, Leishmania, Naegleria fowleri, Plasmodium falciparum, Plasmodium vivax, Plasmodium ovale, Plasmodium malariae, Plasmodium knowlesi, Rhinosporidium seeberi, Sarcocystis bovihominis, Sarcocystis suihominis, Toxoplasma gondii, Trichomonas vaginalis, Trypanosoma brucei, Trypanosoma cruzi, Taenia multiceps, Diphyllobothrium latum, Echinococcus granulosus, Echinococcus multilocularis, Echinococcus vogeli, Echinococcus oligarthrus, Hymenolepis nana, Hymenolepis diminuta, Taenia saginata, Taenia solium, Bertiella mucronata, Bertiella studeri, Spirometra erinaceieuropaei, Clonorchis sinensis, Clonorchis viverrini, Dicrocoelium dendriticum, Fasciola hepatica, Fasciola gigantica, Fasciolopsis buski, Gnathostoma spinigerum, Gnathostoma hispidum, Metagonimus yokogawai, Opisthorchis viverrini, Opisthorchis felineus, Clonorchis sinensis, Paragonimus westermani, Paragonimus africanus, Paragonimus caliensis, Paragonimus kellicotti, Paragonimus skrjabini, Paragonimus uterobilateralis, Schistosoma* sp., *Schistosoma mansoni, Schistosoma haematobium, Schistosoma japonicum, Schistosoma mekongi, Echinostoma echinatum, Trichobilharzia regenti, Ancylostoma duodenale, Angiostrongylus costaricensis, Anisakis, Ascaris* sp., *Ascaris lumbricoides, Baylisascaris procyonis, Brugia malayi, Brugia timori, Dioctophyme renale, Dracunculus medinensis, Enterobius vermicularis, Enterobius gregorii, Halicephalobus gingivalis, Loa loa filaria, Mansonella streptocerca, Onchocerca volvulus, Strongyloides stercoralis, Thelazia californiensis, Thelazia callipaeda, Toxocara canis, Toxocara cati, Trichinella spiralis, Trichinella britovi, Trichinella nelsoni, Trichinella nativa, Trichuris trichiura, Trichuris vulpis, Wuchereria bancrofti, Archiacanthocephala, Moniliformis moniliformis, Linguatula serrata, Tunga penetrans, Dermatobia hominis, Cimex lectularius, Pediculus humanus, Pediculus humanus corporis, Pthirus pubis, Demodex folliculorum, Demodex brevis, Demodex canis, Sarcoptes scabiei, Cochliomyia hominivorax,* or *Pulex irritans*. In another embodiment, the target DNA sequence is from a species of a parasite genus selected from the group consisting of *Angiostrongylus, Demodex, Thelazia, Dirofilaria,* and *Acantocheilonema*. Particularly, the target DNA sequence is from a parasite species selected from the group consisting of *Angiostrongylus vasorum, Demodex canis, Demodex cornei, Demodex injai, Demodex cati, Demodex gatoi, Dirofilaria immitis, Dirofilaria repens, Acantocheilonema dracunculoides,* and *Thelazia callipaeda.*

In a preferred embodiment, the target DNA sequence is a sequence from *Leishmania*, preferably a sequence selected from a species of the group consisting of *L. aethiopica, L. amazonensis, L. arabica, L. archibaldi, L. aristedes, L. braziliensis, L. chagasi, L. colombiensis, L. deanei, L. donovani, L. enriettii, L. equatorensis, L. forattinii, L. garnhami, L. gerbili, L. guyanensis, L. herreri, L. hertigi, L. infantum, L. killicki, L. lainsoni, L. major, L. mexicana, L. naiffi, L. panamensis, L. peruviana, L. pifanoi, L. shawl, L. turanica, L. tropica* and *L. venezuelensis*; more preferably selected from a species of the group consisting of *L. aethiopica, L. braziliensis, L. chagasi, L. donovani, L. infantum, L. major, L. mexicana* and *L. tropica*. In a more preferred embodiment, the target DNA sequence is from *Leishmania infantum*.

In another embodiment, the target DNA sequence is a fungal (e.g. yeast) DNA sequence. For example, the fungal DNA sequence can be found, without limitation, in *Candida* spp. (e.g. *Candida albicans*), *Aspergillus* (e.g. *Aspergillus fumigatus, Aspergillus flavus, Aspergillus clavatus*), *Cryptococcus* (e.g. *Cryptococcus neoformans, Cryptococcus lau-*

*rentii, Cryptococcus albidus, Cryptococcus gattii), Histoplasma capsulatum, Pneumocystis carinii* or *Stachybotrys chartarum*.

In another embodiment, the target DNA sequence is a mammalian DNA sequence (e.g. human, cows, horses, pigs, sheep, goats, dogs, cats, rodents, etc.). For example, the mammalian DNA sequence can be a sequence found in circulating tumour cells, epithelial cells, or fibroblasts.

The term "sample", as used herein, includes a biological sample (e.g. blood, bone marrow, urine, saliva, sputum, lymph, plasma, ejaculate, lung aspirate, cerebrospinal fluid and biopsy without limitation) and a sample from an environmental source. Biological samples include, without limitation, animal or human samples, liquid and solid food and feed products (dairy items, vegetables, meat, etc.). Preferred biological samples include, without limitation, any biological fluid, cell, tissue, organ or portion thereof that contains DNA. Preferably, the biological sample is selected from lesional swab, throat swab, nasal swab, vaginal swab and rectal swab. A biological sample can include a neoplastic cell. Said sample can be from any organism and includes, but is not restricted to, bacteria, fungi, viruses, plants, animals, e.g. human beings, non-human primates, reptiles, insects, birds, worms, fish, mammals, domestic and farm animals (cows, horses, pigs, sheep, goats, dogs, cats, rodents, etc.). In a particular embodiment the sample is from an organism different than the organism from which the target DNA sequence originates. In an embodiment, the sample is from a mammal selected from dogs, cats, rodents, preferably rats and hamsters. In a preferred embodiment the sample is from a dog. In another embodiment the sample is from a human being. Environmental samples include, without limitation, surface matter, soil, water and industrial samples, as well as samples obtained from food and dairy processing instruments. The sample being analysed can be derived from a single source (e.g. a single organism, tissue, cell, etc.) or be a pool of DNA from a plurality of organisms, tissues or cells. Said sample can be obtained by conventional methods. Extraction of DNA from the sample may be carried out by methods well known by the person skilled in the art.

In a first step, the method for detecting a target DNA sequence according to the first method of the invention involves submitting the sample DNA to recombinase-polymerase isothermal nucleic acid amplification.

The term "recombinase-polymerase isothermal nucleic acid amplification" (also known as RPA), as used herein, refers to the isothermal amplification method operating best at constant temperatures between 37-42° C. that employs three core enzymes: a recombinase, a single-stranded DNA-binding protein (SSB) and a strand-displacing polymerase. The RPA method comprises the following steps: (i) first, a recombinase is contacted with a first and a second nucleic acid primers to form a first and a second nucleoprotein primers; (ii) second, the first and second nucleoprotein primers are contacted to a double stranded target sequence to form a first double stranded structure at a first portion of said first strand and form a double stranded structure at a second portion of said second strand so the 3' ends of said first nucleic acid primer and said second nucleic acid primer are oriented towards each other on a given template DNA molecule; and the single-stranded DNA binding protein binds to displaced strands of DNA to prevent the primers from being displaced; (iii) third, the 3' end of said first and second nucleoprotein primers are extended by a strand-displacing DNA polymerase to generate first and second double stranded nucleic acids, and first and second displaced strands of nucleic acids, and (iv) finally, the second and third steps are repeated until a desired degree of amplification is reached. No thermal or chemical melting is required to initiate amplification and the reaction progresses typically within 5-10 minutes. A description of the RPA technique may be found on European patent EP 1 759 012 B1.

Suitable conditions for carrying out the RPA can be found on the materials and methods section and can be determined by the person skilled in the art. In a preferred embodiment, the RPA is carried out at a temperature of 37° C.

The RPA of the first method of the invention is performed in the presence of a pair of primers capable of specifically amplifying the target DNA sequence wherein the first primer is labelled at the 5' end with a gold nanoparticle and the second primer is labelled at the 5' end with a first member of a binding pair.

The term "primer" as used herein, refers to a short strand of nucleic acid that is complementary to a sequence in another nucleic acid and serves as a starting point for DNA synthesis. Preferably, the primer has at least 5, at least 6, at least 7, at least 8, at least 9, at least 10, at least 11, at least 12, at least 13, at least 14, at least 15, at least 16, at least 18, at least 20, at least 25, at least 30 or more bases long. More preferably, the optimum length is between 30-35 bases long.

The expression "capable of specifically amplifying", as used herein, means that the primer is designed to be complementary to the target DNA sequence to be amplified, (i.e. refers to the base pairing that allows the formation of a duplex between the primer and its complementary sequence in a DNA molecule). Complementary nucleotides are, generally, A and T (or A and U), or C and G. Two single-stranded DNA molecules are said to be substantially complementary when the nucleotides of one strand, optimally aligned and compared and with appropriate nucleotide insertions or deletions, pair with about 60% of the other strand, at least 70%, at least 80%, at least 85%, usually at least about 90% to about 95%, and even about 98% to about 100%. The degree of identity between two nucleotide regions is determined using algorithms implemented in a computer and methods which are widely known by the persons skilled in the art. The identity between two nucleotide sequences is preferably determined using the BLASTN algorithm (BLAST Manual, Altschul, S. et al., NCBI NLM NIH Bethesda, Md. 20894, Altschul, S., et al., J., 1990, Mol. Biol. 215:403-410). The primers hybridize to the target DNA sequence. "Hybridization" refers to the process in which two single-stranded polynucleotides bind non-covalently to form a stable double-stranded polynucleotide.

The expression "specifically", when referred to the amplification of a target DNA sequence by a pair of primers, means that the primers are capable of hybridizing to an amplify the target DNA sequence but they are not capable of hybridizing and amplifying other sequences different from the target DNA sequence, thus allowing a specific detection of said sequence.

Primers suitable for the methods of the invention are primers without long tracks of guanines at the first 3-5 nucleotides of the 5' end and without unusual sequence elements such as homopolymers. The preferred primers have GC content between 30% and 70%. In order to improve performance, primers having cytidines at the 5' end and guanines and cytidines at the last 3 nucleotides of the 3' end are preferred. The amplicon length preferably does not exceed from 500 bp. The ideal amplicon length is between 100-200 bp.

The first primer of the first method of the invention is labelled at the 5' end with a gold nanoparticle. The term "5' end", as used herein, designates the end of a nucleotide strand that has the fifth carbon in the sugar-ring of the deoxyribose at its terminus. The expression "gold nanoparticle" or "AuNP", as used herein, refers to an ultrafine particle between 2 and 200 nm in size that is formed by gold atoms. In a preferred embodiment gold nanoparticles have 20 nm in size. Gold nanoparticles suitable for the present invention are gold nanoparticles obtained by a simple method of synthesis, having a narrow size distribution, capable of being easily conjugated to antibodies and/or ssDNA and having electro(catalytic) activity. Generally, gold nanoparticles are produced in a liquid by reduction of chloroauric acid. Different methods are known by the person skilled in the art to manufacture gold nanoparticles. In a preferred embodiment the method used is Turkevich's method (Turkevich et al. Discuss. Faraday Soc. 1951, 11:55-75) that is disclosed in section 3.2 of the experimental part of the present description. In order to label the 5' end of the first primer with a gold nanoparticle said primer has to be previously modified with thiol groups and then the AuNPs/primer conjugate can be obtained. A method for modifying the first primer with thiol groups and conjugating it with AuNPs is disclosed in section 3.3 of Examples. FIG. 3(b) shows a scheme of the synthesis of AuNPs and their conjugation with primers.

The second primer of the first method of the invention is labelled at the 5' end with a first member of a binding pair. In an embodiment, the second primer used in step a) of the first method of the invention is not bound to the second member of the binding pair conjugated to magnetic beads. In another embodiment, the second primer used in step a) of the first method of the invention is bound to the second member of the binding pair conjugated to magnetic beads.

The term "binding pair", in the context of the first method of the invention, refers to a pair formed by a first member and a second member and includes any of the class of immune-type binding pairs, such as antigen/antibody (for example, digoxigenin/anti-digoxigenin antibody) or hapten/anti-hapten systems; and also any of the class of non-immune-type binding pairs which include systems wherein the two components share a natural affinity for each other but are not antibodies, such as biotin/avidin, biotin/streptavidin, folic acid/folate binding protein and protein A or G/immunoglobulins. The second primer is labelled with a first member of a binding pair by methods well known in the art.

In an embodiment, the first member of a binding pair is an antigen or hapten. The term "antigen", as used herein, refers to any substance which provokes an adaptative immune response. The term "hapten", as used herein, refers to a small molecule that changes the structure of an antigenic epitope and that has to be attached to a large carrier molecule such as a protein to induce an immune response.

In another embodiment, the first member of a binding pair is biotin.

In an embodiment, the second member of the binding pair is an antibody specific for the antigen or hapten of the first member of the binding pair. The term "specific", in the context of the antibody used in the first method of the invention, means that said antibody is capable of recognizing a particular antigen and no other different antigens.

In another embodiment, the second member of a binding pair is streptavidin.

The second member of the binding pair can complex with the first member of the binding pair. Said second member of the binding pair is conjugated to magnetic beads.

The term "magnetic beads", as used herein, refers to magnetic particles having a size between 0.5 to 500 µm that are uniform particles having magnetic properties when placed in a magnetic field and with no residual magnetism once removed from the magnetic field. Such particles commonly contain magnetic elements such as iron, nickel and cobalt and their chemical compounds. The magnetic beads can be paramagnetic or super-paramagnetic. In an embodiment, magnetic beads are super-paramagnetic. Magnetic beads are preferably spherical. In some embodiments, magnetic beads having a true spherical shape and defined surface chemistry are used to minimize chemical agglutination and non-specific binding. In a preferred embodiment, magnetic beads have a size lower than 2.8 µm, preferably lower than 2.5 µm, more preferably lower than 2.0 µm, even more preferably lower than 1.5 µm, even more preferably lower than 1.0 µm. In an embodiment the magnetic beads have a size of 1.0 µm.

Magnetic beads and methods for their preparation are well-known and they are widely available commercially, with or without functional groups capable of binding to affinity molecules. Suitable magnetic beads are commercially available such as from Dynal Inc. (Lake Success, N.Y.); PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.). In particular embodiments, magnetic particles are MyOne™ Dynabeads® magnetic beads (Dynal Inc.).

The term "conjugated", as used herein, means that the second member of a biding pair is coupled to the surface of the magnetic bead. Said modified magnetic beads may be manufactured by methods well known by the person skilled in the art or may be commercially available.

The first member of the binding pair may be bound to the second member of a binding pair before or after the amplification takes place.

If the first member of the binding pair is bound to the second member of the binding pair before the amplification takes place, this means that the second primer is modified with magnetic beads. A method for obtaining a primer modified with magnetic beads is described in section 3.7 of Material and methods and FIG. 5. The experimental section shows that if the second primer is modified with magnetic beads said magnetic beads must have a size lower than 2.8 µm and must separate from the region of the primer that recognizes the target DNA sequence by a polynucleotide spacer. Preferably, when the second primer is modified with magnetic beads the second member of the binding pair is not an antibody. This design allows reducing time and cost of the analysis of the amplified product. Therefore, in an embodiment the second primer labelled at the 5' end with a first member of a binding pair is bound to the second member of the binding pair conjugated to magnetic beads before step a) takes place, and wherein said magnetic beads have a size lower than 2.8 µm and are separated from the region of the primer that recognizes the target DNA sequence by a polynucleotide spacer.

The expression "polynucleotide spacer", as used herein, refers to a nucleotide sequence that links the region of the primer that recognizes the target DNA sequence and the magnetic bead and which acts as a hinge region, providing space between both elements and assuring that the amplification process is not affected by the presence of the magnetic bead. The polynucleotide spacer may be of any length that allows accomplishing said functions. In a preferred embodiment, the polynucleotide spacer is a nucleotide sequence with a length of 10-30 nucleotides, preferably 15-20 nucleotides, more preferably has a length of 15 nucleotides. In an embodiment, the polynucleotide spacer is the sequence ATATATATATATATA (SEQ ID NO: 5).

If the first member of the binding pair is bound to the second member of the binding pair after the amplification takes place, this means that the amplified product labelled with a first member of a binding pair is captured after amplification by a second member of the binding pair. Therefore, in an embodiment the second member of the binding pair conjugated to magnetic beads is added after step a). This embodiment is described in section 3.6 of Material and methods and FIG. 4.

In an embodiment, the method for detecting a target DNA sequence according to the first method of the invention involves capturing the amplification products obtained in step a) in the presence of a magnetic bead conjugated to a second member of a binding pair before step b) takes place.

The expression "amplification product", as used herein, refers to a double strand amplicon wherein the first strand is labelled at the 5' end with a gold nanoparticle and the second strand is labelled at the 5' end with a first member of a binding pair.

The expression "in the presence of a magnetic bead", as used herein, means that a magnetic bead is associated to the second strand of the amplified product either because the second member of the binding pair conjugated to magnetic beads is added after step a) or because the second primer labelled at the 5' end with a first member of a binding pair is bound to the second member of the binding pair conjugated to magnetic beads before step a) takes place.

The presence of a magnetic bead associated to the amplification product is necessary to recover said product from the reaction mixture. This capture is performed by magnetic separation of the products associated to the magnetic beads.

When the second primer labelled at the 5' end with a first member of a binding pair is bound to the second member of the binding pair conjugated to magnetic beads before step a) takes place, the product obtained in step a) is washed for removing the excess of primers before step b) takes place. Therefore, in an embodiment, the product obtained in step a) is washed for removing the excess of primers before step b) takes place.

In a second step (step b), the method for detecting a target DNA sequence according to the first method of the invention involves measuring the electrochemical signal produced by the gold nanoparticles forming part of the amplification products obtained in step a) using a screen-printed carbon electrode after capture of the amplification products on the electrode using magnetic beads conjugated to a second member of a binding pair.

In this final step the captured magnetic beads associated to the amplification product are placed on the surface of a screen-printed carbon electrode that has a magnet attached to the reverse side of the surface. Gold nanoparticles are detected taking advantage of their electroactive properties. In a preferred embodiment the electrocatalytic activity of gold nanoparticles towards the electroreduction of hydrogen ions in an acidic media is approached for their sensitive detection. In order to measure the electrochemical signal produced by the captured products, a solution of HCl is added, and a potential is applied to reduce $H^+$ ions to $H_2$ due to the catalytic effect of the gold nanoparticles. Quantitative measurements may be performed according to the disclosure of section 3.8 of Materials and methods.

The expression "electrochemical signal", as used herein, refers to the absolute value of the current registered at 100 seconds when a potential of −1.00 V was applied in chronoamperometric mode.

The expression "biosensor", as used herein, refers to an analytical device used for the detection of the amplified product that combines a biological component (the sensitive biological element that recognizes the amplified product under study, i.e. the second member of a binding pair conjugated to magnetic beads) with a physicochemical detector (electrochemical transducer) that transforms the signal resulting from the interaction of the amplified product with the biological element into another signal more easily measured and quantified. The biosensor of the present invention must capture the magnetic beads and therefore, it is made from a metallic material.

Figure 2:
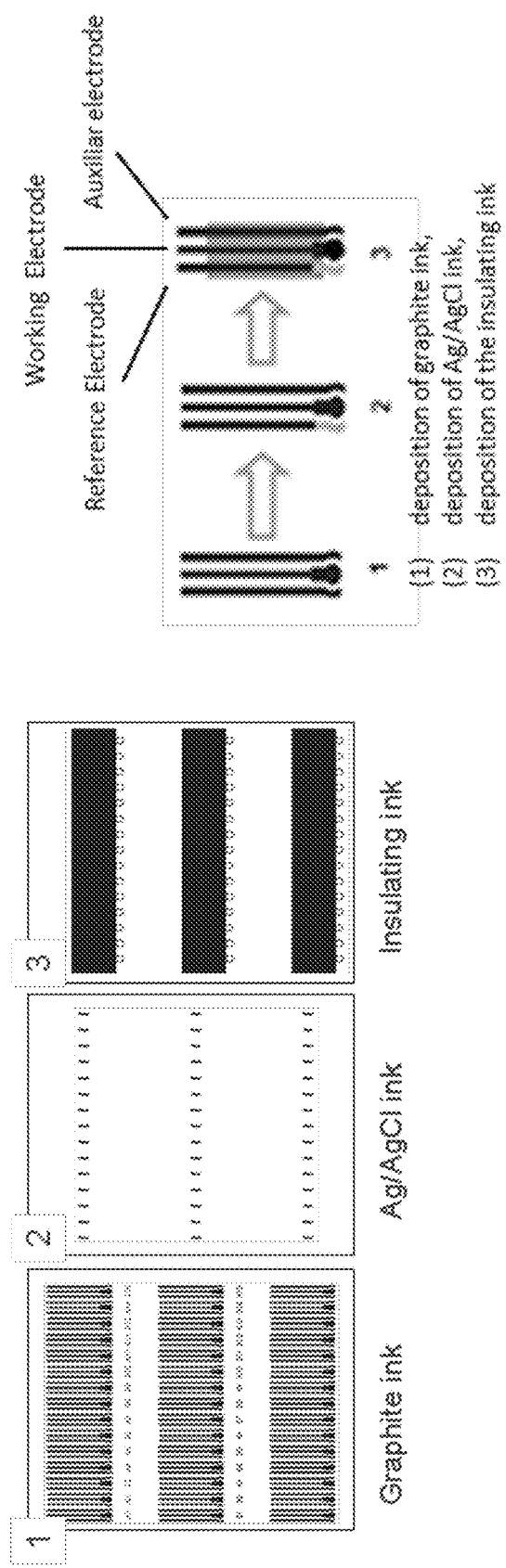
FIG. 2. Up: Design of the masks used for the preparation of screen-printing electrodes. The different inks printed on a polyester sheet and detail of how these inks are placed in a single sensor. Down: Pictures of a polyester sheet with 45 printed sensors, detail of one single sensor and picture of the electrochemical set-up using a portable potentiostat.
Figure 2:
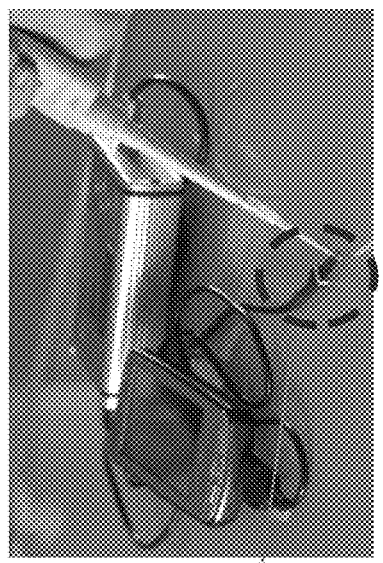
Figure 2:
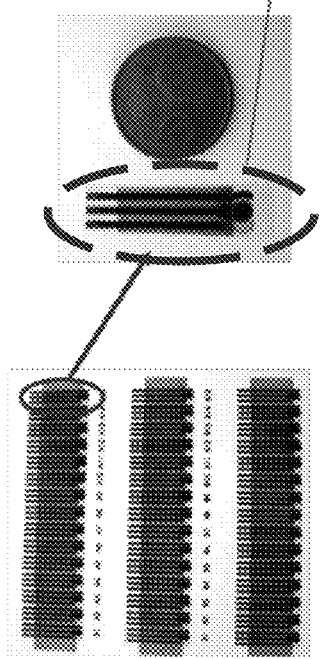

The electrochemical transducer (or electrode) is a screen-printed carbon electrode (SPCE) which includes a carbon working electrode, a carbon counter electrode and a silver/silver chloride reference electrode. SPCE and their manufacture methods are well known in the state of the art. A method for manufacturing SPCEs is described in section 3.1 of Material and methods wherein disposable SPCEs that require the use of only 25 µl of sample have been manufactured. FIG. 2 shows details of this procedure. In a preferred embodiment the screen-printed carbon electrode is printed on a polyester sheet.

In the first method of the invention the detection of an electrochemical signal superior to the background signal indicates the presence of the target DNA sequence in the sample. The background signal corresponds to the absolute value of the current (recorded at 100 seconds) by the $H^+$ ions reduction in the absence of gold nanoparticles.

The electrochemical signal is proportional to the quantity of gold nanoparticles and, consequently, to the concentration of the amplified product.

Second Method of the Invention

In a second aspect, the invention relates to an in vitro method (hereinafter referred to as "second method of the invention") for detecting a target DNA sequence in a sample comprising the following steps:

a) submitting the sample DNA to a recombinase-polymerase isothermal nucleic acid amplification in the presence of a pair of primers capable of specifically amplifying the target DNA sequence wherein the first primer is labelled at the 5' end with a first member of a first binding pair and the second primer is labelled at the 5' end with a first member of a second binding pair, and wherein said first members of the first and second binding pairs do not substantially cross-react with any second member of any different binding pair, and b) measuring the electrochemical signal produced by the gold nanoparticles forming part of the amplification products obtained in step a) using a screen-printed carbon electrode after the first member of a first binding pair is bound to a second member of a first binding pair conjugated to a gold nanoparticle and after capture of the amplification products on the electrode using magnetic beads conjugated to a second member of a second binding pair wherein the detection of an electrochemical signal superior to the background signal indicates the presence of the target DNA sequence in the sample.

The terms disclosed in steps a) and b) of the second method of the invention have been defined previously in the context of the first method of the invention.

The RPA of step a) of the second method of the invention is performed in the presence of a pair of primers capable of specifically amplifying the target DNA sequence wherein the first primer is labelled at the 5' end with a first member of a first binding pair and the second primer is labelled at the 5' end with a first member of a second binding pair and wherein said first members of the first and second binding pairs do not substantially cross-react with any second member of any different binding pair.

The term "binding pair" has been defined previously in the context of the first method of the invention.

In the second method of the invention both primers are labelled with a first member of a binding pair, but the first member of the first binding pair cannot be the same as the first member of the second binding pair; and the second member of the first binding pair cannot be the same as the second member of the second binding pair. Additionally, the first members of the first and second binding pairs do not substantially cross-react with a second member of a different binding pair, i.e. the first member of the first binding pair cannot be substantially bound to the second member of the second binding pair and vice versa. The expression "do not substantially cross-react", as used herein, refers to an amount of binding or recognizing between molecules in an assay mixture under particular assay conditions wherein the second member of the first binding pair is capable of binding or recognizing the first member of the first binding pair and is substantially incapable of binding or recognizing the first member of the second binding pair. Substantial or lack of substantial cross-reaction can be tested using a number of widely known methods, e.g. an enzyme-linked immunosorbent assay (ELISA) or a Western blot assay, or a radioimmunoassay (RIA) or an immunohistochemical assay.

In a preferred embodiment the first member of the first binding pair is an antigen or hapten. Preferably, said hapten is fluorescein isothiocyanate (FITC). In a preferred embodiment the second member of the first binding pair is an antibody specific for the antigen or hapten of the first member of the first binding pair.

In a preferred embodiment the first member of the second binding pair is biotin and the second member of the second binding pair is a biotin-binding molecule.

The expression "biotin-binding molecule", as used herein, refers to any molecule capable of binding to biotin. Preferred biotin-binding molecules include streptavidin and avidin, as well as derivatives and analogues thereof (e.g. nitro-streptavidin) and also antibodies recognizing biotin. In a more preferred embodiment, the biotin-binding molecule is streptavidin.

In an embodiment, the second member of the second binding pair conjugated to magnetic beads is added after step a).

In another embodiment, the second primer labelled at the 5' end with a first member of a second binding pair is bound to the second member of the second binding pair conjugated to magnetic beads before step a) takes place, and wherein said magnetic beads have a size lower than 2.8 µm and are separated from the region of the primer that recognizes the target DNA sequence by a polynucleotide spacer.

In an embodiment, the method for detecting a target DNA sequence according to the second method of the invention involves capturing the amplification products obtained in step a) in the presence of a magnetic bead conjugated to a second member of a second binding pair before step b) takes place.

The expression "amplification product", in the context of the second method of the invention, refers to a double strand amplicon wherein the first strand is labelled at the 5' end with a first member of a first binding pair and the second strand is labelled at the 5' end with a first member of a second binding pair.

The expression "in the presence of a magnetic bead", as used herein, means that a magnetic bead is associated to the second strand of the amplified product either because the second member of the second binding pair conjugated to magnetic beads is added after step a) or because the second primer labelled at the 5' end with a first member of a second binding pair is bound to the second member of the second binding pair conjugated to magnetic beads before step a) takes place.

The presence of a magnetic bead associated to the amplification product is necessary to recover said product from the reaction mixture. This capture is performed by magnetic separation of the products associated to the magnetic beads.

When the second primer labelled at the 5' end with a first member of a second binding pair is bound to the second member of the second binding pair conjugated to magnetic beads before step a) takes place, the product obtained in step a) is washed for removing the excess of primers before step b) takes place. Therefore, in an embodiment, the product obtained in step a) is washed for removing the excess of primers before step b) takes place.

The second method of the invention involves an additional step, wherein the product obtained in step a) is captured with a second member of a first binding pair conjugated to a gold nanoparticle.

The product obtained in step a) of the second method of the invention is a double stranded amplicon wherein the first strand is labelled at the 5' end with a first member of a binding pair and the second strand is associated to a magnetic bead. This product is recovered from the mixture obtained in step a) by interaction with a second member of a first binding pair conjugated to a gold nanoparticle.

The term "conjugated", in the context of step b) of the second method of the invention means that the second member of the first binding pair is coupled to the surface of a gold nanoparticle.

In a preferred embodiment, the product obtained in step a) of the second method of the invention is washed for removing the excess of the second member of a first binding pair conjugated to a gold nanoparticle before step b) takes place.

Step b) of the second method of the invention is the same as step b) of the first method of the invention.

The embodiments of the first method of the invention disclosed above are applicable to the second method of the invention.

Particularly, in an embodiment the target DNA sequence is from a pathogen, preferably from the Kinetoplastea class, more preferably *Leishmania* and even more preferably is *L. infantum*. In another embodiment the target DNA sequence is a sequence of the kinetoplast. In another embodiment the sample is from a dog. In another embodiment the recombinase-polymerase isothermal nucleic acid amplification is carried out at a temperature of about 37° C.

KITS OF THE INVENTION

The invention also includes kits for carrying out the methods according to the invention.

The term "kit", as used in the present document, refers to a combination of a set of reagents suitable for detecting a target DNA by a method according to the invention together with one or more types of elements or components (for example, other types of biochemical reagents, containers, packaging suitable for its commercial sale, substrates to which the reagents are bound, electronic hardware components, etc.).

The invention relates to kits for carrying out the first method of the invention wherein one of the primers is labelled with a gold nanoparticle and the other primer is associated to magnetic beads.

In an aspect, the invention relates to a kit (hereinafter referred to as "first kit of the invention") comprising a pair of primers capable of specifically amplifying a target DNA sequence wherein the first primer is labelled at the 5' end with a gold nanoparticle and the second primer is labelled at the 5' end with a first member of a binding pair, and the first member of a binding pair is bound to a second member of a binding pair conjugated to magnetic beads, and wherein said magnetic beads have a size lower than 2.8 µm and are separated from the region of the primer that recognizes the target DNA sequence by a polynucleotide spacer.

The invention also relates to kits for carrying out the first method of the invention wherein the magnetic beads conjugated to a second member of a binding pair are provided separated from the primer originally used in the amplification step.

In an aspect, the invention relates to a kit (hereinafter referred to as "second kit of the invention") comprising
(i) a pair of primers capable of specifically amplifying a target DNA sequence wherein the first primer is labelled at the 5' end with a gold nanoparticle and the second primer is labelled at the 5' end with a first member of a binding pair, and
(ii) a second member of a binding pair conjugated to magnetic beads.

In an embodiment of the first and second kits of the invention the first member of a binding pair is an antigen o hapten, preferably biotin. In another embodiment of the first and second kits of the invention the second member of the binding pair is an antibody specific for said antigen. In another embodiment of the first and second kits of the invention the second member of a binding pair is streptavidin.

In an embodiment of the first and second kits of the invention the magnetic beads are superparamagnetic microbeads.

In an embodiment of the first and second kits of the invention the kit further comprises at least a reagent selected from a recombinase, a single-stranded DNA binding protein and a strand-displacing DNA polymerase.

The term "recombinase", as used herein, refers to an enzyme that can coat single-stranded DNA (ssDNA) to form filaments, which can then scan double-stranded DNA (dsDNA) for regions of sequence homology. When homologous sequences are located, the nucleoprotein filament (comprising the recombinase) strand invades the dsDNA creating a short hybrid and a displaced strand bubble known as a D-loop. Suitable recombinase agents include the E. coli RecA protein, the T4 uvsX protein, or any homologous protein or protein complex from any phyla. Eukaryotic RecA homologues are generally named Rad51 after the first member of this group to be identified. Other non-homologous recombinases may be utilized in place of RecA, for example as Red or RecO. Recombinase agents generally require the presence of ATP, ATPγS, or other nucleoside triphosphates and their analogs. Naturally, any derivatives and functional analogs of the recombinase above may also function itself as a recombinase and these derivatives and analogs are also contemplated in the present invention. For example, a small peptide from RecA, which has been shown to retain some aspects of the recombination properties of RecA, may be used.

The term "single-stranded DNA binding protein", as used herein, refers to a protein that binds to single-stranded DNA, melt secondary structure, facilitate outgoing strand displacement, and suppress branch migration. Examples of single-stranded DNA binding proteins useful for the invention are, without limitation, E. coli SSB and bacteriophages T4 gp32.

The term "strand-displacing DNA polymerase", as used herein, refers to a DNA polymerase having the ability to displace downstream DNA encountered during synthesis. Examples of strand-displacing DNA polymerases are, without limitation, E. coli polymerase II or III, E. coli polymerase V and φ29 polymerase.

In another embodiment of the first and second kits of the invention the kit further comprises a screen-printed carbon electrode.

If the target DNA sequence is a sequence from the kinetoplast of L. infantum, an embodiment of the first and second kits of the invention is a kit wherein the pair of primers capable of specifically amplifying the target DNA sequence are primers of sequence SEQ ID NO: 1 and SEQ ID NO: 2.

The terms disclosed in this section have been defined in the context of the first, and second methods of the invention.

The embodiments of the first and second methods of the invention disclosed above are applicable to the kits of the invention.

Particularly, in an embodiment the target DNA sequence is from a pathogen, preferably from the Kinetoplastea class, more preferably Leishmania, even more preferably L. infantum. In another embodiment the target DNA sequence is a sequence of the kinetoplast.

OLIGONUCLEOTIDES OF THE INVENTION

The invention also discloses oligonucleotides to be used in the methods of the invention and to be included in kits.

In an aspect the invention relates to an oligonucleotide whose sequence is selected from the group consisting of SEQ ID NO: 1 and SEQ ID NO: 2, In a preferred embodiment said oligonucleotide is labelled at the 5' end with a gold nanoparticle or with a first member of a binding pair.

DIAGNOSTIC METHODS OF THE INVENTION

The methods of the present invention for detecting a target DNA sequence in a sample allow diagnosing an infection by a pathogen in a subject.

In an aspect, the invention relates to an in vitro method for diagnosing an infection by a pathogen in a subject comprising detecting the presence of a target DNA sequence from said pathogen in a biological sample of said subject by a method according to the invention.

In the context of the present invention, "in vitro method for diagnosing an infection" is understood as a method which allows showing the existence of an infection in a subject by means of detecting the presence of a target DNA sequence from an infectious pathogen in a sample isolated from the subject.

The term "infection" or "infectious disease", as used herein, refers to the invasion of a host organism by an infectious agent such as viruses, viroids and prions, microorganisms such as bacteria, nematodes such as roundworms and pinworms, arthropods, fungi and parasites.

The term "pathogen", as used herein, refers to an infectious agent such as viruses, viroids and prions, microorganisms such as bacteria, nematodes such as roundworms and pinworms, arthropods, fungi and parasites. Exemplary pathogens are disclosed in the context of the first method of the invention.

"Subject" in the present invention is understood as any animal, preferably an animal classified as mammal and includes but is not limited to domestic and farm animals, primates and humans, for example human beings, non-human primates, cows, horses, pigs, sheep, goats, dogs, cats or rodents. Preferably, the subject is a female or male human being of any race or age. Most preferably, the subject is a dog. In the context of the present invention, the subject is a subject who potentially suffers from an infection caused by a pathogen.

The term "biological sample", as used herein, refers to animal or human samples including, without limitation, any biological fluid (blood, bone marrow, plasma, serum, bronchoalveolar washing fluid, urine, nasal secretion, ear secretion, urethral secretion, cerebrospinal fluid, pleural fluid, synovial fluid, peritoneal fluid, sputum, lymph, plasma, ejaculate, lung aspirate, etc.), cell, tissue, organ or portion thereof that contains DNA. Preferably, the biological sample is selected from lesional swab, throat swab, nasal swab, vaginal swab and rectal swab. A biological sample can include a neoplastic cell. Said samples can be obtained by conventional methods, using processes known in the state of the art by the person skilled in the art.

All the embodiments of the first and second methods of the invention disclosed above are applicable to the diagnostic methods of the invention.

The present invention is also directed to:

[1]. An in vitro method for detecting a target DNA sequence in a sample comprising the following steps:
  a) submitting the sample DNA to a recombinase-polymerase isothermal nucleic acid amplification in the presence of a pair of primers capable of specifically amplifying the target DNA sequence wherein the first primer is labelled at the 5' end with a gold nanoparticle and the second primer is labelled at the 5' end with a first member of a binding pair, and
  b) measuring the electrochemical signal produced by the gold nanoparticles forming part of the amplification products obtained in step a) using a screen-printed carbon electrode after capture of the amplification products on the electrode using magnetic beads conjugated to a second member of a binding pair,
  wherein the detection of an electrochemical signal superior to the background signal indicates the presence of the target DNA sequence in the sample.

[2]. An in vitro method for detecting a target DNA sequence in a sample comprising the following steps:
  a) submitting the sample DNA to a recombinase-polymerase isothermal nucleic acid amplification in the presence of a pair of primers capable of specifically amplifying the target DNA sequence wherein the first primer is labelled at the 5' end with a first member of a first binding pair and the second primer is labelled at the 5' end with a first member of a second binding pair, and wherein said first members of the first and second binding pairs do not substantially cross-react with any second member of any different binding pair, and
  b) measuring the electrochemical signal produced by the gold nanoparticles forming part of the amplification products obtained in step a) using a screen-printed carbon electrode after the first member of a first binding pair is bound to a second member of a first binding pair conjugated to a gold nanoparticle and after capture of the amplification products on the electrode using magnetic beads conjugated to a second member of a second binding pair
  wherein the detection of an electrochemical signal superior to the background signal indicates the presence of the target DNA sequence in the sample.

[3]. The method according to [1] or [2], wherein:
  (i) if the detection is carried out by a method according to [1], the second primer labelled at the 5' end with a first member of a binding pair is bound to the second member of the binding pair conjugated to magnetic beads before step a) takes place, and wherein said magnetic beads have a size lower than 2.8 µm and are separated from the region of the primer that recognizes the target DNA sequence by a polynucleotide spacer, and
  (ii) if the detection is carried out by a method according to [2], the second primer labelled at the 5' end with a first member of a second binding pair is bound to the second member of the second binding pair conjugated to magnetic beads before step a) takes place, and wherein said magnetic beads have a size lower than 2.8 µm and are separated from the region of the primer that recognizes the target DNA sequence by a polynucleotide spacer.

[4]. The method according to [1] to [3], wherein:
  (i) if the detection is carried out by a method according to [1], the second member of the binding pair conjugated to magnetic beads is added after step a), and
  (ii) if the detection is carried out by a method according to [2], the second member of the second binding pair conjugated to magnetic beads is added after step a).

[5]. The method according to [1] to [4], wherein:
  (i) if the detection is carried out by a method according to [1], the first member of a binding pair is biotin and the second member of a binding pair is streptavidin, and
  (ii) if the detection is carried out by a method according to [2], the first member of the first binding pair is fluorescein isothiocyanate (FITC) and the second member of the first binding pair is an antibody specific for said antigen and, wherein the first member of the second binding pair is biotin and the second member of the second binding pair is streptavidin.

[6]. The method according to [1] to [5], wherein the target DNA sequence is from *Leishmania*.

[7]. The method according to [1] to [6], wherein the target DNA sequence is a sequence of the kinetoplast.

[8]. A kit selected from the group consisting of:
  a) a kit comprising a pair of primers capable of specifically amplifying a target DNA sequence wherein the first primer is labelled at the 5' end with a gold nanoparticle and the second primer is labelled at the 5' end with a first member of a binding pair, and the first member of a binding pair is bound to a second member of a binding pair conjugated to magnetic beads, and wherein said magnetic beads have a size lower than 2.8 µm and are separated from the region of the primer that recognizes the target DNA sequence by a polynucleotide spacer; and
  b) a kit comprising:
    (i) a pair of primers capable of specifically amplifying a target DNA sequence wherein the first primer is labelled at the 5' end with a gold nanoparticle and the second primer is labelled at the 5' end with a first member of a binding pair, and (ii) a second member of a binding pair conjugated to magnetic beads.

[9]. An in vitro method for diagnosing an infection by a pathogen in a subject comprising detecting the presence of a target DNA sequence from said pathogen in a biological sample of said subject by a method according to [1] to [7].

[10]. An oligonucleotide whose sequence is selected from the group consisting of SEQ ID NO: 1 and SEQ ID NO: 2.

The following examples are provided as merely illustratives and are not to be construed as limiting the scope of the invention.

Examples

Materials and Methods
1. *Leishmania* Isothermal Amplification
1.1. Design and Screening of Primer Sets for *Leishmania* Assay Initially, 3 candidate primers for kinetoplast and 8 candidate primers for Intergenic Spacer region (ITS1) of *Leishmania* were designed following recommended conditions [optimum length between 30-35 nt; without long tracks of guanines at the 5' end (first 3-5 nucleotides) and 'unusual' sequence elements such as homopolymers; with a GC content between 30% and 70% and preferably with cytidines at the 5' end and guanines and cytidines at the 3' end of the primer (last 3 nucleotides) to improve performance]. Amplicon length must not exceed about 500 bp, and ideally must be between 100-200 bp.

All possible combinations of primers were tested using standard conditions of TwistAmp® kits (TwistDX) (37° C. of reaction temperature; magnesium-acetate concentrations of 14 mM; shaking 4' after initiation of the reaction; 480 nM of each primer).

Parameters that can be modified by the user [reaction temperature (37° C.-42° C.), magnesium concentration (12 mM and 20 mM), agitation regime (3'-6' after initiation of the reaction) and primer concentrations (150 nM-600 nM)] were adjusted to obtain the best performance.

This first step generated 4 sets of primers used in simplified standard conditions (37° C. of reaction temperature, 14 mM of magnesium concentration, 480 nM of primer concentration, without agitation 4' after starting the reaction and with a reaction time of 20').

The kinetoplast region was chosen due to the higher intensity obtained in an agarose gel after selected target amplification.
1.2. Secondary Primer Screen for *Leishmania* Assay To improve the performance of the *Leishmania* kinetoplast assay a 'second generation' of primers was designed by creating variants of the best primer set identified in the first step (moving 1 base pair around the initial primer) and re-screened the new candidates to improve amplification performance.

Primers set selected at last were:

```
                                               (SEQ ID NO: 1)
K6F   CTTTTCTGGTCCTCCGGGTAGGGGCGTTCTG (31 bp)

(SEQ ID NO: 2)
K3R   CCACCCGGCCCTATTTTACACCAACCCCCAGTTTCCC (37 bp)
``` that amplified a fragment of approximately 140 base pair length.

Figure 3:
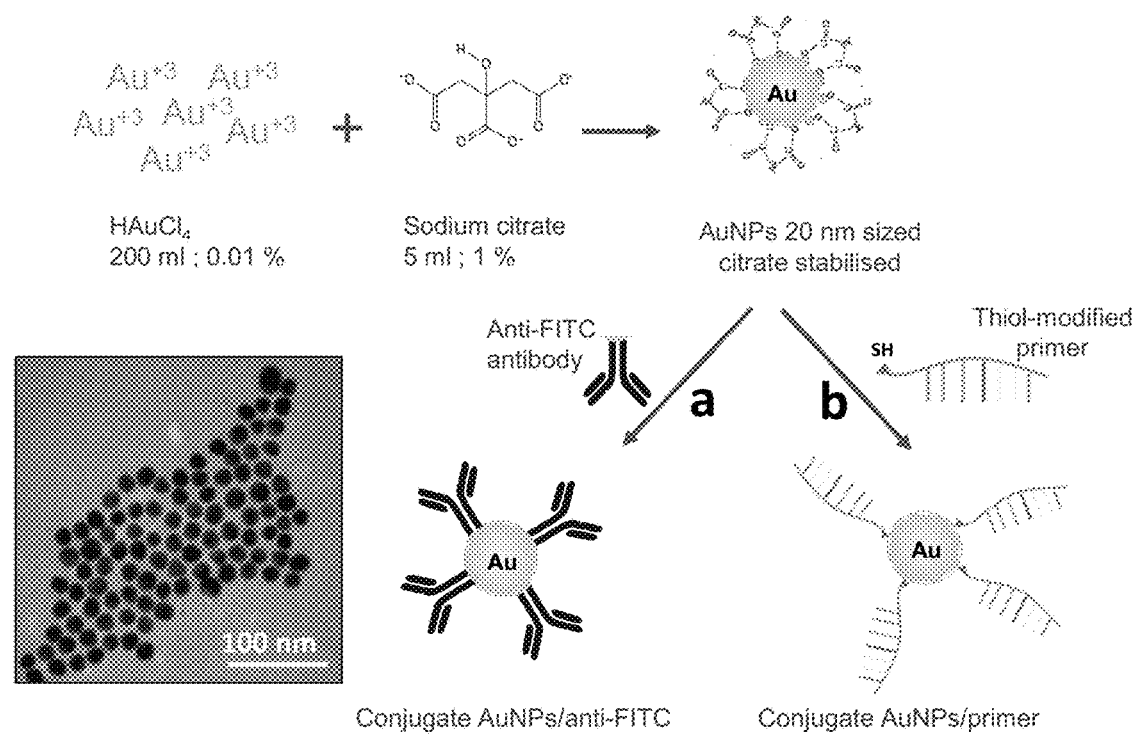
FIG. 3. Scheme of the experimental procedure followed for the AuNPs synthesis and conjugation with: (a) anti-FITC antibodies and (b) thiol-modified primer. TEM image corresponds to a suspension of the 20-nm AuNPs obtained.

Primer concentration was adjusted to 300 nM and the reaction time was decreased up to 10'. Under these conditions the limit of detection was <1 parasite in the reaction (analyzed in agarose gel electrophoresis) (FIG. 1).
2. Preparation of Gold Nanoparticles Gold nanoparticles (AuNP) 20 nm sized and stabilized by citrate were prepared using the Turkevich's method (Turkevich et al. Discuss. Faraday Soc. 1951, 11:55-75). Briefly, 50 mL aqueous solution of 0.1% $HAuCl_4$ were heated to boiling and vigorously stirred in a 250 mL round-bottom flask; 1.25 mL of sodium citrate 1% were added quickly to this solution. Boiling was continued for additional 10 min. The solution was cooled to room temperature with a continuous stirring. The colloids were stored in dark bottles at 4° C. All glassware used in this preparation was previously cleaned in aqua regia overnight and rinsed with double distilled $H_2O$. Reflux was used for all the procedure.
3. Electrochemical Detection
3.1. Screen-Printed Carbon Electrodes (SPCE) Fabrication The electrochemical transducers used for the nanoparticle label detection were homemade screen-printed carbon electrodes (SPCEs), consisting of three electrodes: working electrode WE, reference electrode RE and counter electrode CE in a single strip. The full size of the sensor strip was 29 mm×6.7 mm, and the WE diameter was 3 mm. The fabrication of the SPCEs was carried out in three steps. First, a graphite layer was printed onto the polyester sheet, using the screen-printing machine with the stencil (where it is the electron pattern). After curing for 15 minutes at 95° C., an Ag/AgCl layer was printed and cured for 15 minutes at 95° C. Finally, the insulating ink was printed and cured at 95° C. for 20 minutes. FIG. 2 shows details of this procedure as well as of the obtained sensors.
3.2. Gold Nanoparticles Synthesis Gold nanoparticles were synthesized as described in section 2.A scheme of the AuNPs synthesis procedure as well as a TEM image is shown in FIG. 3.
3.3. Gold Nanoparticles Conjugation with Thiol-Modified Primers The conjugation of AuNPs to primers already modified with thiol groups was performed adapting the procedure disclosed in Storhoff et al. [Storhoff, J J., Elghanian, R., Mucic, R C., Mirkin, C A., Letsinger, R L. One-pot colorimetric differentiation of polynucleotides with single base imperfections using gold nanoparticle probes. J. Am. Chem. Soc. 120 (1998): 1959-1964]. 190 μL of AuNPs suspension were mixed with 10 μL of 1500 μg/mL thiolated primer solution and incubated for 20 h at 25° C. with agitation (250 rpm) (final concentration of primer: 75 μg/mL). After that, this solution was added to 50 μL of 10 mM phosphate buffer (pH 7)/0.1M NaCl and allowed to stand for 44 h. Finally, a centrifugation at 14000 rpm for 20 min at 4° C. was carried out, and AuNPs/primer conjugates were reconstituted in 200 μL of milli-Q™ water (FIG. 3, pathway b).
3.4. Gold Nanoparticles Conjugation with Anti-FITC Antibodies The conjugation of AuNPs to anti-FITC antibodies, was performed according to the following procedure [Ambrosi, A., Castaneda, M T., Killard, A. J., Smyth, M R., Alegret, S., Merkogi, A. Double-codified gold nanolabels for enhanced immunoanalysis. Analytical Chemistry, 79 (2007) 5232-5240]: 2 mL of AuNPs suspension were mixed with 100 μL of 100 μg/mL of antibody solution and incubated for 20 min at 25° C. with agitation (650 rpm). Subsequently, a blocking step with 150 μL of 1 mg/ml BSA, incubating for 20 min at 25° C. with agitation (650 rpm) was undertaken. Finally, a centrifugation at 14000 rpm for 20 min at 4° C. was carried out, and AuNPs/anti-FITC conjugates were reconstituted in milli-Q™ water.

3.5. Zeta Potential Measurements

A 1 µL suspension of AuNPs, AuNPs/primer and of AuNPs/amplified DNA was diluted in 1 mL of PBS buffer, vortexed, and transferred into a 4 mL polystyrene cuvette (FB55143, Fisher Scientific). The data were collected and analyzed with the Dispersion Technology software 4.20 (Malvern) producing diagrams for the zeta potential as a distribution versus total counts.

3.6. Magnetic Capturing of the Isothermally Amplified Product Already Labelled with Gold Nanoparticles The isothermally amplified product was already labelled with gold nanoparticles, since one of the primers was connected with AuNPs as detailed in section 3.3. 10 µL of the streptavidin-modified magnetic beads (MBs) suspension (100 µg) were mixed with 90 µL of B&W buffer. After washing 2 times with B&W, the suspension was re-suspended in 50 µL of B&W and 50 µL of the isothermally amplified product (labelled with thiol and AuNPs) were added and then incubated for 30 min at 25° C. with agitation (650 rpm). During this incubation, the isothermally amplified product was captured by the MBs through the streptavidin-biotin interaction. "Positive" (amplified DNA from dogs with *Leishmania*) and "blank" samples (amplified DNA from healthy dogs) were assayed.

The rest of reagents in solution (excess of primers, etc.) were removed by washing with B&W (2 times), PBS buffer (2 times) and milli-Q™ water in order to remove the excess of AuNPs-FITC. The final complex was re-suspended in milli-Q™ water.

Figure 4:
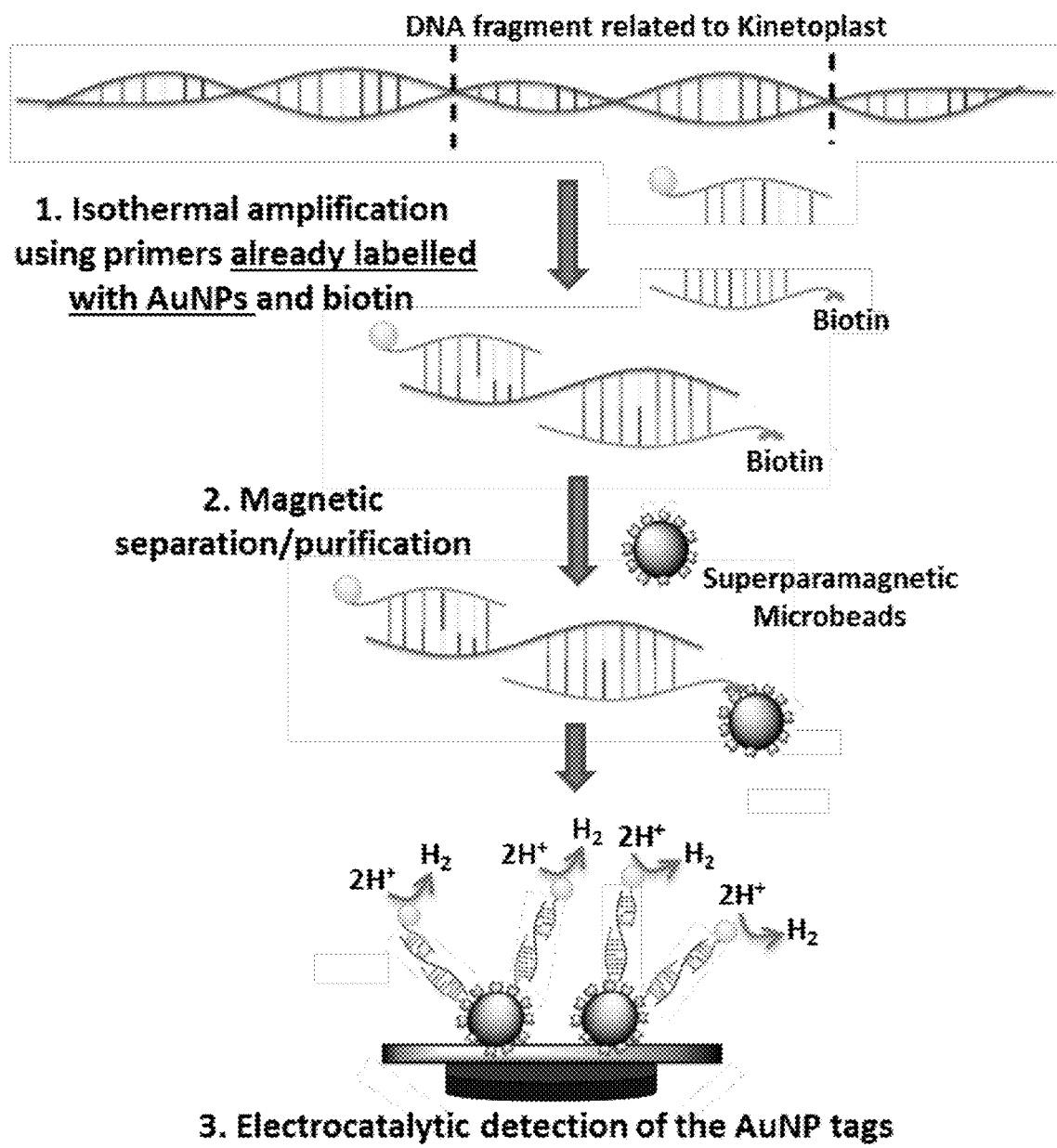
FIG. 4. Scheme of the experimental procedure for isothermal amplification using primers labelled with AuNPs and biotin (step 1), magnetic capturing of the isothermally amplified product (step 2) and electrocatalytic detection (step 3).

A scheme of this procedure together with a picture of the magnetic separation platform and a SEM image of the MBs is shown in FIG. 4 (steps 2-3).

3.7. Integration of Magnetic Beads Before Amplification

Figure 5:
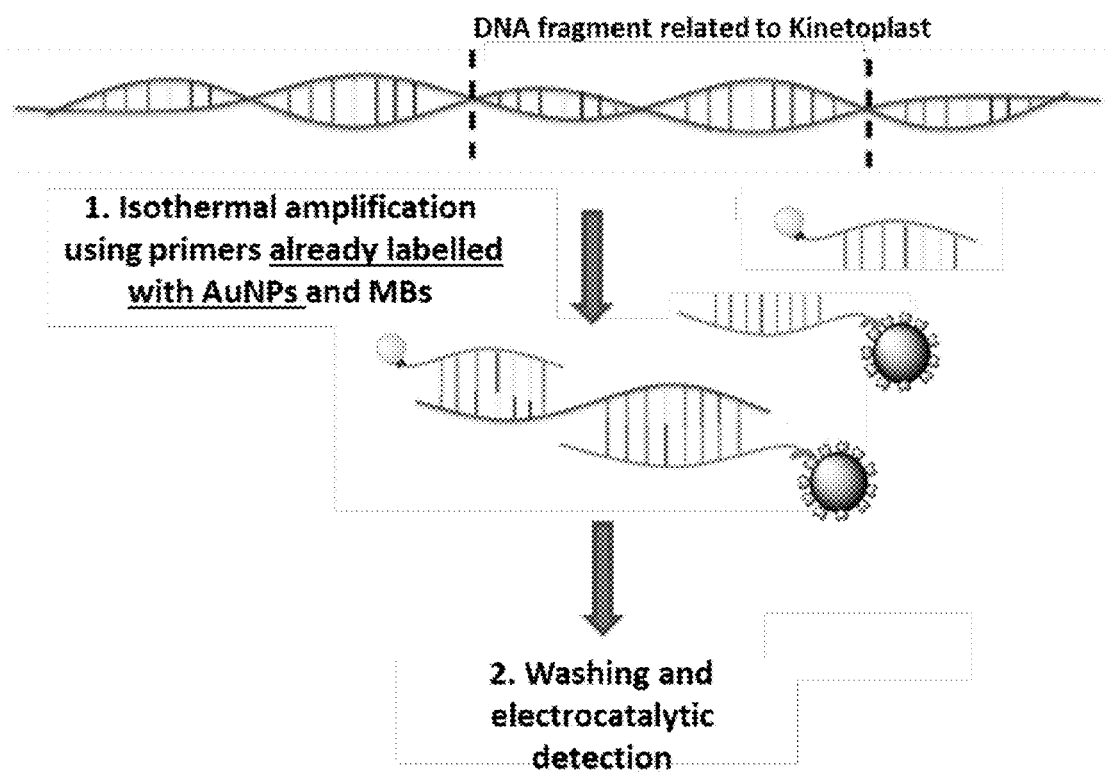
FIG. 5. Scheme of the experimental procedure for the detection of isothermally amplified DNA using primers labelled with AuNPs and MBs.

MBs were connected with one of the primers through the streptavidin-biotin interaction, following this experimental procedure: (i) incubation of the MBs (50 µL; 1 mg/mL) with biotinylated primer (15 µL; 100 µM) (30 min; 25° C.); (ii) washing and re-suspending in 15 µL of water; (iii) addition of 2.4 µL. of the complex MBs/primer to the isothermal amplification reagents mixture. A scheme of the experimental procedure for the detection of isothermally amplified DNA using primers labelled with gold nanoparticles and MBs is shown in FIG. 5.

3.8. Electrochemical Detection

25 µL of the MBs complex suspension were placed on the working area of the SPCE (connected to the potentiostat and where it was previously attached a hard plastic base with a magnet on the reverse side of the working area). After 30 seconds, 25 µL of 2M HCl solution were added and a potential of +1.35 V was applied during 1 min (electrochemical pre-treatment). After that, a potential of −1.00 V was applied during 100 seconds in chronoamperometric mode. Under these conditions, the $H^+$ ions were reduced to $H_2$ thanks to the catalytic effect of the AuNPs labels. The absolute value of the current registered at 100 seconds was considered as the analytical signal, being this value proportional to the quantity of AuNPs and, consequently, to the concentration of isothermally amplified product. A scheme of the electrocatalytic reduction of $H^+$ ions by the AuNPs is shown in the last step of FIG. 4.

Results

Specificity of the Assay with Commercial Lateral Flow Detection

Lateral flow detection was performed using the Milenia® HybriDetec 2 T. Detection was performed using 5 µl of 1/20 dilution in milli-Q™ water of the amplification product in 100 µl of the running buffer, as manufacturer's instructions.

Figure 6:
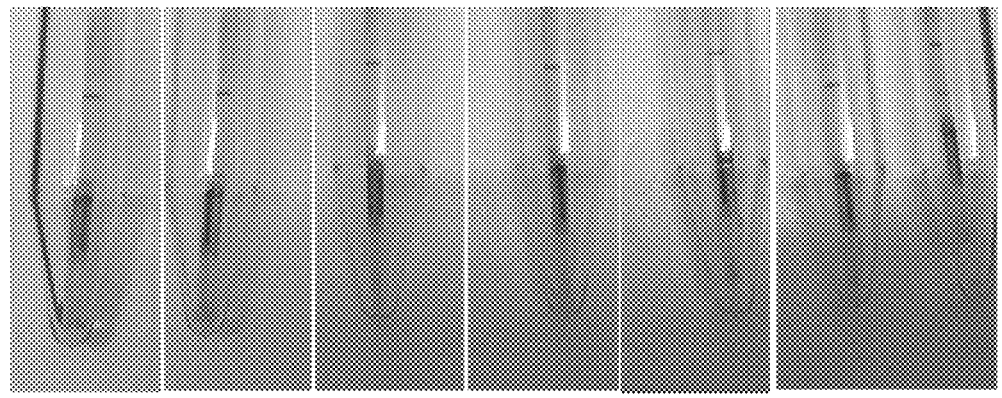
FIG. 6. Lateral flow results of the specificity assay with other pathogens. NTC: negative template control.
Figure 6:
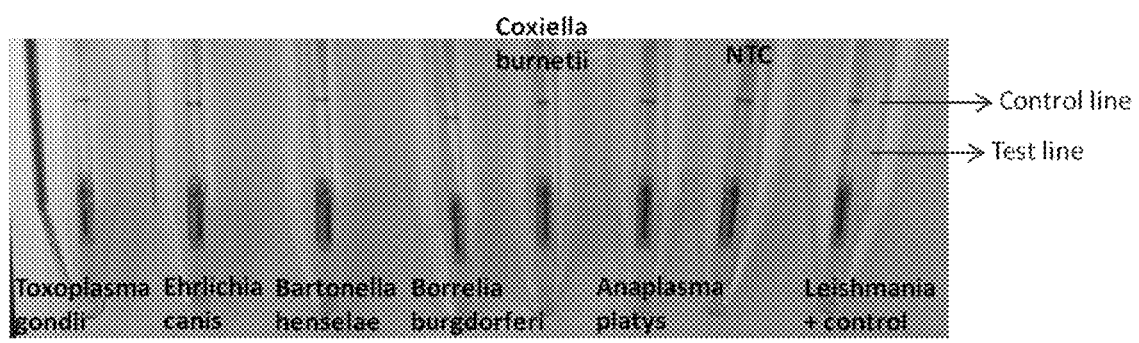

Specificity was tested (i) in silica, (ii) sequencing the positive control and (iii) performing a cross-amplification study in which amplification with specific primers was performed over all the positives of other pathogens that could be in co-infection, mostly CVBD (Canine Vector Borne Diseases) (FIG. 6). Expected results are amplification of the specific positive sample and no amplification of any of the other pathogens tested. DNA of positive control of CVBD was obtained from commercial slides from Megacor coated with cells infected with the pathogens (*Ehrlichia canis*, *Babesia gibsoni*, *Rickettsia rickettsii*, *Rickettsia conorii*, *Rickettsia fells*, *Rickettsia typhi*, *Bartonella henselae* and *Anaplasma platys*) or commercial DNA from Genekam Biotechnology AG (*Borrelia burgdorferi*, *Coxiella burnetii* and *Toxoplasma gondii*).

The assay of the inventors has 100% specificity.

Quantitative Real Time *Leishmania* PCR Comparison

Results were compared with those obtained by quantitative real time amplification using the PCR described by Francino et al (Francino et al. 2006. Veterinary Parasitology 137(3-4):214-221) (Table I).

TABLE I

Results of parasitemia of different samples obtained by quantitative real time PCR (qPCR).

| sample | qPCR Ct | Parasites/µl DNA | Parasites/ml blood |
|--------|---------|------------------|--------------------|
| 1 | 37.6 | 0.0018 | 0.5 |
| 2 | 35.2 | 0.0074 | 1.88 |
| 3 | 33.5 | 0.0206 | 5.15 |
| 4 | 30.2 | 0.146 | 36.5 |
| 5 | 27.8 | 0.606 | 151.68 |

Figure 7:
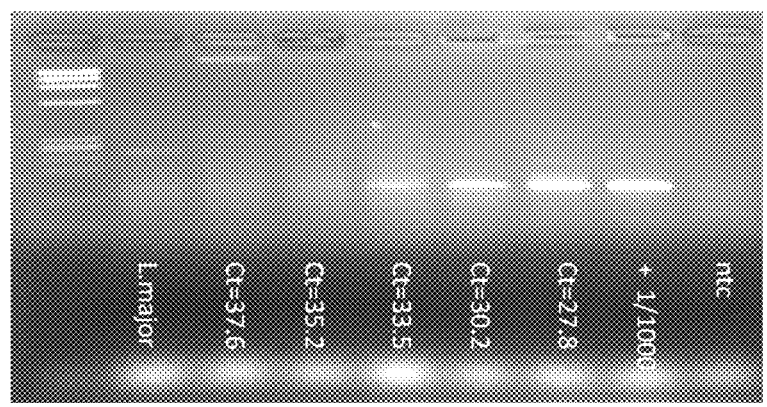
FIG. 7. Results of parasitemia of different samples obtained by isothermal amplification and agarose gel electrophoresis detection.

An analysis by isothermal amplification of the same DNAs analysed by qPCR with different parasitemia levels was performed. Isothermal amplification amplified without problems DNAs with 0.02 parasites/pi detected by agarose gel electrophoresis (FIG. 7).

Quantitative Analysis and Estimation of the Limit of Detection

Figure 8:
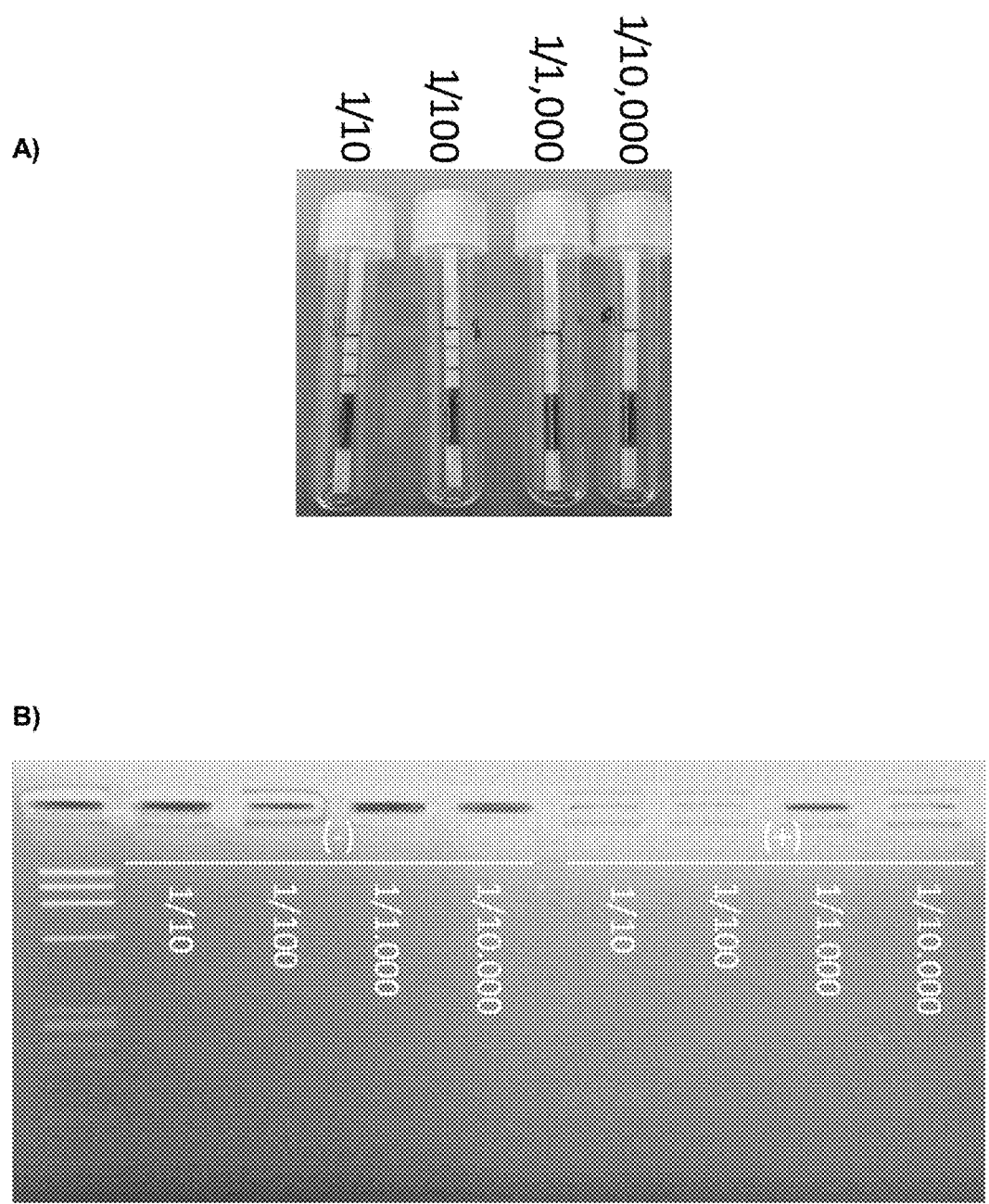
FIG. 8. Limit of detection using commercial lateral flow (A) or agarose gel electrophoresis (B).

Serial dilutions of an isothermal amplified product starting with 1.5 parasites in the isothermal reaction were performed. Results showed that lateral flow (FIG. 8, panel A) is more sensitive than agarose gel electrophoresis (FIG. 8, panel B) for detection. Three fold of sensitivity (1/10,000 versus 1/10) was gained (FIG. 8).

The limit of detection was estimated by evaluating amplified products prepared from samples containing different concentrations of spiked parasites. 20 ng of dog DNA with different amounts of parasite were spiked to finally perform the isothermal amplification starting with 20 parasites in the assay, followed by 4 parasites, 2 parasites, 0.4 parasites, 0.2 parasites, 0.04 parasites and 0.02 parasites. The limit of detection with the commercial lateral flow assay was of 0.2 parasites in the isothermal amplification.

Zeta Potential Characterization of AuNP-Labelled Primers and Amplified DNA

Zeta potential is an easily measurable technique, recently reported as an efficient tool for the monitoring and analysis of modifications on the surface of NPs, with minimal sample preparation [F. Thielbeer, K. Donaldson, M. Bradley, Bioconj. Chem. 2011, 22, 144-150]. It has been used to obtain information concerning the particle surface charge, chemical modifications and also stability of colloid suspensions. A high zeta potential (positive or negative; typically higher than 10 mV) confers stability since the dispersion resists aggregation.

Since ssDNA is negatively charged, the conjugation of AuNPs with ssDNA should give rise to negative charged conjugates which would shift the Z potential to more negative values.

All these characteristics make zeta potential an ideal technique for the characterization of both the primers and the final amplified DNA labelled with AuNPs.

Figure 9:
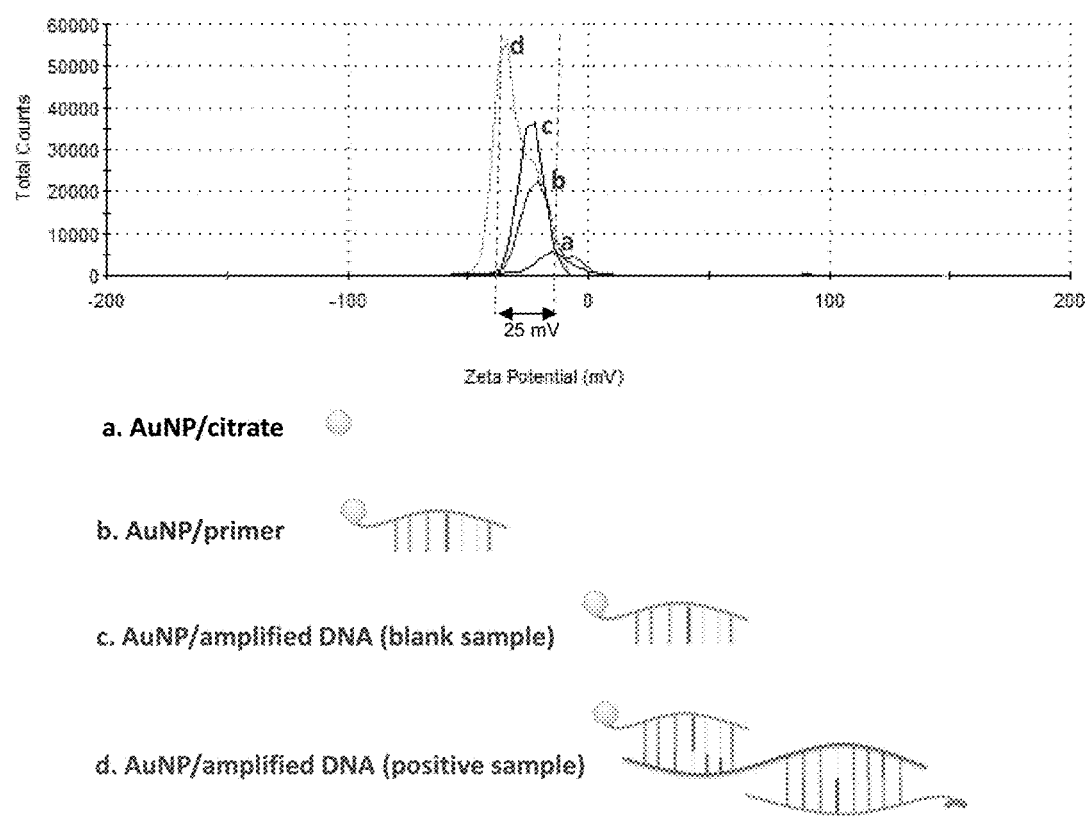
FIG. 9. Diagram for the zeta potential as a distribution versus total counts for a dispersion of AuNPs before (a curve) and after (b curve) the conjugation with the primer and for amplified DNA using the AuNP-labelled primer for a positive (d curve) and a blank (c curve) sample.

As can be observed in FIG. 9, a gradual shift to more negative values was observed in the Zeta potential of AuNPs when higher was the coverage degree by ssDNA. This suggests that AuNPs were being loaded with negative charged molecules that is the case of ssDNA. First, a shift from the value of the non-modified AuNPs (a) was observed for the AuNP/primer (b) indicating that the primer was correctly connected with the AuNP. After the amplification, this shift was up to 25 mV (d), suggesting the covering of the AuNPs with the amplified DNA that has more negative charges. No significant shift was observed for a control amplification assay performed with a blank sample (c), also corroborating the specificity of the system.

Electrochemical Detection of DNA Amplified Using AuNP-Labelled Primers.

Figure 10:
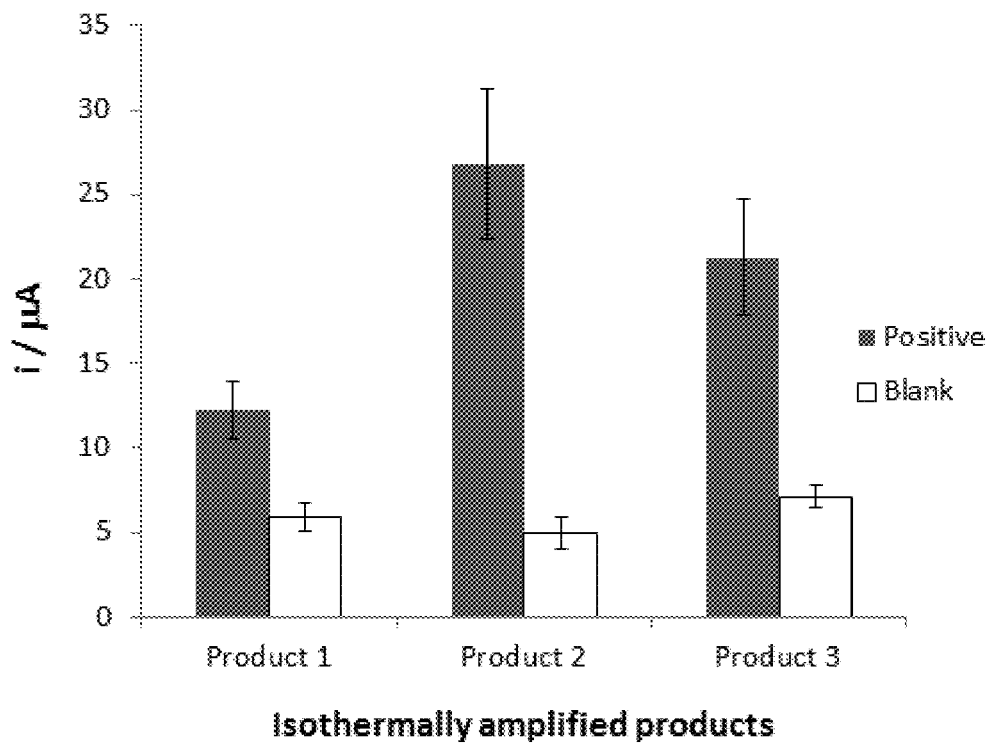
FIG. 10. Comparison of the analytical signals obtained for different "positive" and "blank" samples after DNA amplification using AuNP-labelled primers.

The AuNP-labelled amplified products were electrochemically detected following the above detailed experimental procedure. The electrochemical method exhibited a good reproducibility and sensitivity, allowing to perfectly discriminate amplified DNA from dogs without *Leishmania*, demonstrating the specificity of both the amplification procedure and the electrochemical detection, as shown in FIG. 10.

The stability of the primer labelled with AuNPs is a very important parameter that has been evaluated. A robust method needs to have disposable primers ready to be used in a similar way than the commercially available primers labelled i.e. with biotin or FITC.

Figure 11:
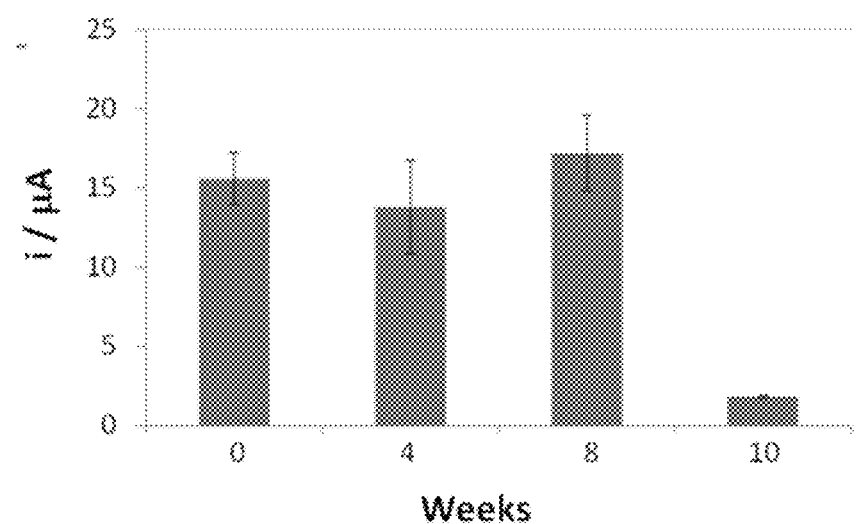
FIG. 11. Analytical signals electrochemically detected obtained for different isothermal amplifications performed several weeks after the preparation of the conjugate of AuNP/primer.

In order to study such stability, a conjugate of AuNP/primer was prepared, stored at 4° C. (protected from light) and used for different isothermal amplifications performed after several weeks. As shown in FIG. 11, the amplification worked well for conjugates prepared up to 8 weeks before. However, any signal was obtained after 10 weeks), indicating that probably the connection between the primer and the AuNPs was broken.

Electrochemical Detection of DNA Amplified Using Both AuNP and MB-Labelled Primers The integration of the MBs also in the primers used for the isothermal amplification was also evaluated, so as to highly simplify this experimental procedure, as detailed in section 3.7.

MBs of two different sizes (the standard ones of 2.8 µm and also smaller commercially available ones of 1 µm) and two different kind of primers were evaluated: the same than used before and also a longer one, containing the same amplification region but including also an spacer, that is a tail of oligonucleotides that helps to keep the magnetic bead far from the amplification zone.

Figure 12:
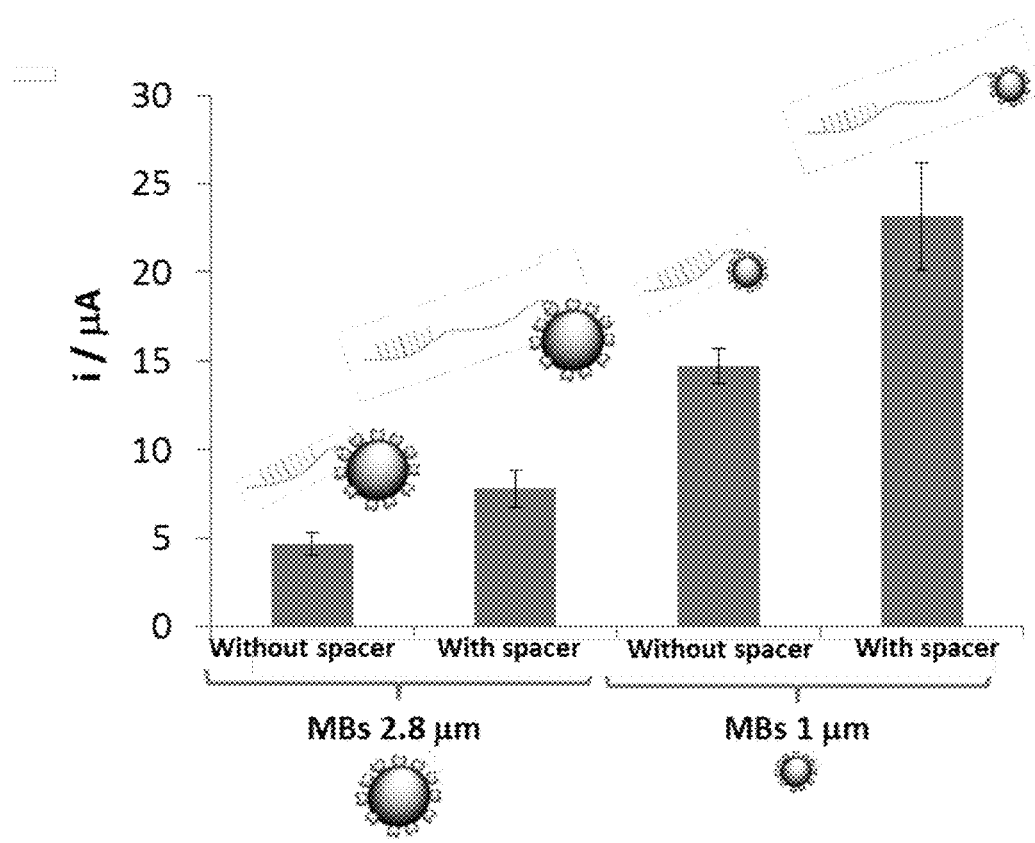
FIG. 12. A) Analytical signals electrochemically detected obtained for different isothermal amplifications performed using different sized MBs and primers with and without spacer. B) SEM characterization of the MBs after the DNA isothermal amplification.
Figure 12:
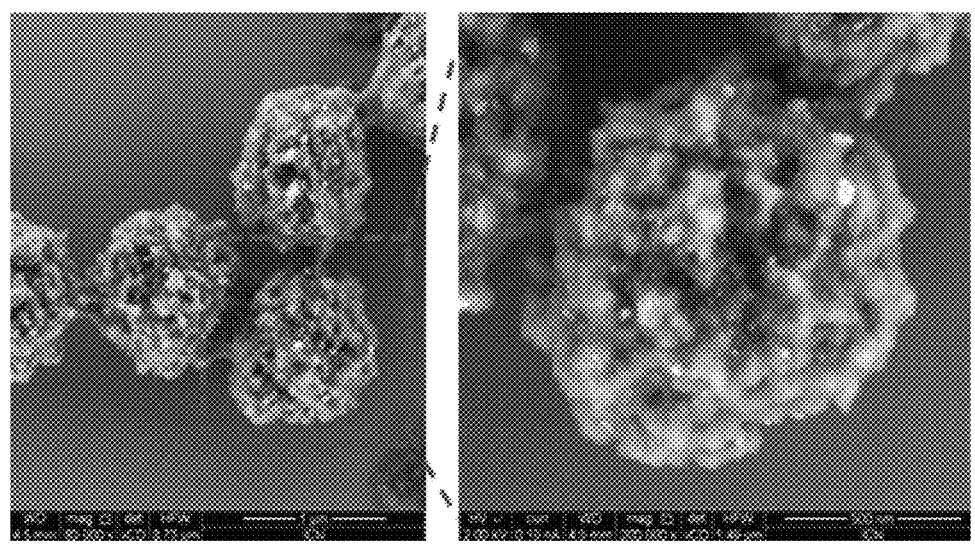

The isothermal amplification was performed using one primer labelled with AuNPs and the other one labelled with the magnetic bead following one of these strategies (different sized MBs and primers) (FIG. 12). In this case, the experimental procedure for the measurement after the amplification is enormously simplified since only a washing step of few seconds is necessary immediately before the electrochemical measurement.

Results seem to indicate that the amplification doesn't work using the bigger MBs in combination with the short primer since the currents recorded are in the levels of the background. The results improved a little bit when the use of longer primers, with the spacer, was introduced. When the smaller MBs and the short primer were tried, the amplification worked in a higher extent, and this was highly improved when it was used in combination with the primers with spacer. So this suggests that the bigger MBs are hindering the amplification, probably due to the beads deposition during the amplification procedure. Furthermore, it is better to have the amplification sequence of the primer not in direct contact with the bead so as to facilitate the amplification.

Figure 13:
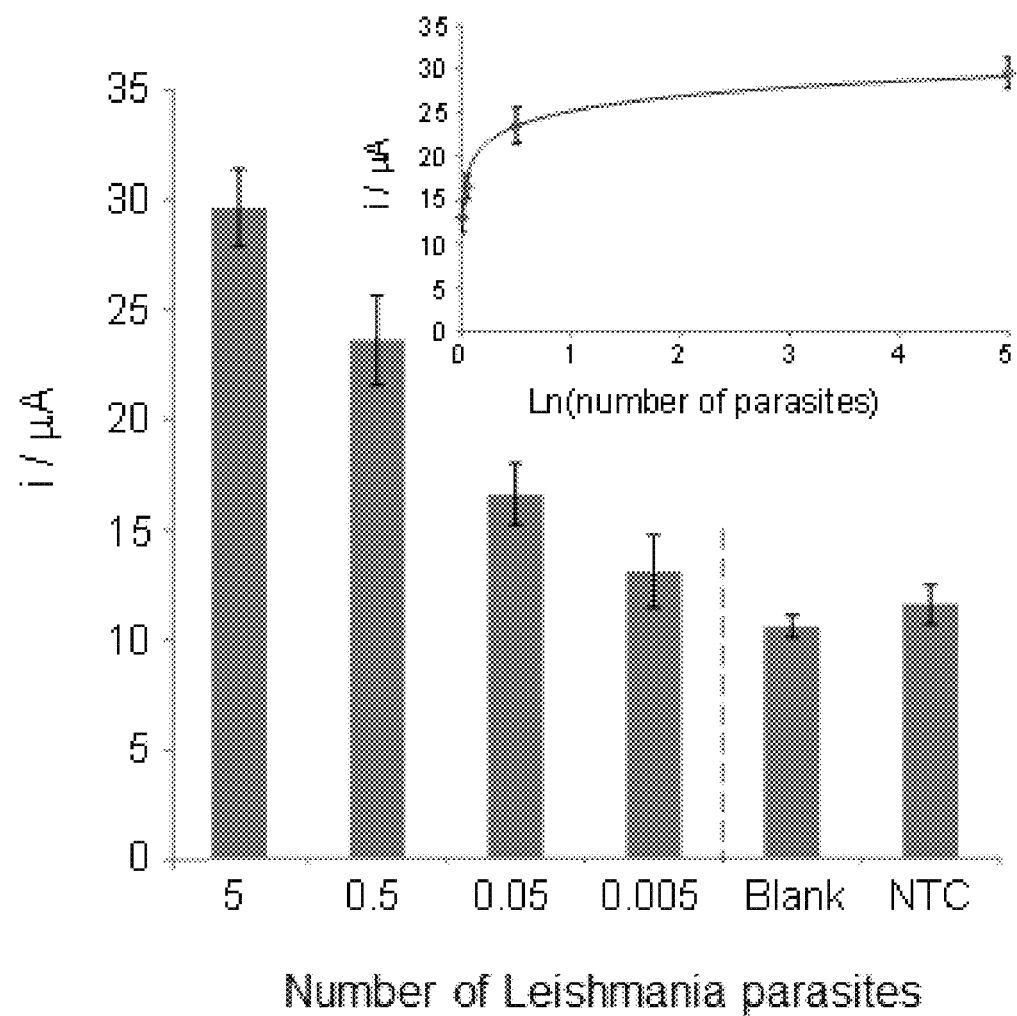
FIG. 13. Quantitative *L. infantum* parasite determination. Analytical signals obtained for double labelled MB-AuNP isothermal amplified DNA products prepared from different quantities of parasites. Inset graphic shows the logarithmic relationship between the number of *Leishmania* parasites and the value of the analytical signal.

The optimized methodology was applied for the evaluation of amplified DNA prepared from samples containing different quantities of spiked parasites. As shown in FIG. 13, a linear relationship between the parasite concentration and the analytical signal was obtained in the range of 0.005 to 5 spiked parasites. A limit of detection (LOD) of 0.004 parasites per DNA amplification reaction was estimated, as the parasite number giving a signal equal to the blank signal plus three times its standard deviation. The reproducibility of responses for 3 spiked parasites was also studied, obtaining a relative standard deviation (RSD) of 7%.

This AuNP/MBs based electrochemical approach results are quite better than those obtained by other POC tests using nucleic acid sequence based amplification (NASBA) and coupled to oligochromatography (OO) for *Leishmania* detection (Mugasa C M. et al. Parasit. Vectors 2010, 3:13) and even much better than the 1 parasite per PCR detection limit offered by the OligoC-Test® (http://www.corisbio.com/Products/Molecular-Field/Leishmania.php). This technique provides a valuable proof of concept since the double MB/AuNP-labelled approach is a universal methodology that can be applied for any isothermal DNA amplification design.

The invention claimed is:

1. An in vitro method for detecting a target DNA sequence in a sample comprising the following steps:
   a) submitting the sample DNA to a recombinase-polymerase isothermal nucleic acid amplification in the presence of a pair of primers capable of specifically amplifying the target DNA sequence wherein the first primer is labelled at the 5' end with a gold nanoparticle and the second primer is labelled at the 5' end with a first member of a binding pair that is bound to the second member of a binding pair conjugated to magnetic beads having a size lower than 2.8 µm before step a) takes place, and
   b) measuring the electrochemical signal produced by the gold nanoparticles forming part of the amplification products obtained in step a) using a screen-printed carbon electrode after capture of the amplification products on the electrode using said magnetic beads conjugated to a second member of a binding pair, wherein the detection of an electrochemical signal superior to the background signal indicates the presence of the target DNA sequence in the sample.

2. The method according to claim 1, wherein the first member of a binding pair is an antigen or hapten and the second member of the binding pair is an antibody specific for said antigen or hapten.

3. The method according to claim 1, wherein the magnetic beads are separated from the region of the primer that recognizes the target DNA sequence by a polynucleotide spacer.

4. The method according to claim 1, wherein the product obtained in step a) is washed for removing the excess of primers before step b) takes place.

5. The method according to claim 1, wherein the first member of a binding pair is biotin and the second member of a binding pair is streptavidin.

6. The method according to claim 1, wherein the target DNA sequence is from a pathogen.

7. The method according to claim 6, wherein the pathogen is an organism from the Kinetoplastea class.

8. The method according to claim 7, wherein the organism from the Kinetoplastea class is *Leishmania*.

9. The method according to claim 8, wherein the *Leishmania* is *Leishmania infantum*.

10. The method according to claim 7, wherein the target DNA sequence is a sequence of the kinetoplast.

11. A kit selected from the group consisting of:
a) a kit comprising a pair of primers capable of specifically amplifying a target DNA sequence wherein the first primer is labelled at the 5' end with a gold nanoparticle and the second primer is labelled at the 5' end with a first member of a binding pair, and the first member of a binding pair is bound to a second member of a binding pair conjugated to magnetic beads, and wherein said magnetic beads have a size lower than 2.8 µm and are separated from the region of the primer that recognizes the target DNA sequence by a polynucleotide spacer; and
b) a kit comprising:
(i) a pair of primers capable of specifically amplifying a target DNA sequence wherein the first primer is labelled at the 5' end with a gold nanoparticle and the second primer is labelled at the 5' end with a first member of a binding pair, and
(ii) a second member of a binding pair conjugated to magnetic beads, wherein said magnetic beads have a size lower than 2.8 µm.

12. The kit according to claim 11 further comprising at least a reagent selected from a recombinase, a single-stranded DNA binding protein and a strand-displacing DNA polymerase.

13. The kit according to claim 11 further comprising a screen-printed carbon electrode.

14. The kit according to claim 11, wherein the target DNA sequence is from *Leishmania*.

15. The kit according to claim 14, wherein the target DNA sequence is a sequence of the kinetoplast.

16. The kit according to claim 11, wherein the pair of primers capable of specifically amplifying the target DNA sequence are primers consisting of sequence SEQ ID NO: 1 and SEQ ID NO: 2.

17. An in vitro method for diagnosing an infection by a pathogen in a subject comprising detecting the presence of a target DNA sequence from said pathogen in a biological sample of said subject by a method according to claim 1.

18. A combination of primers suitable for a method according to claim 1, wherein the sequence of the first primer consists of SEQ ID NO: 1 and the sequence of the second primer consists of SEQ ID NO: 2, and wherein one of said primers is labelled at the 5' end with a gold nanoparticle and the other primer is labeled at the 5' end with a first member of a binding pair.

* * * * *